(12) United States Patent
Shin et al.

(10) Patent No.: US 11,207,257 B2
(45) Date of Patent: Dec. 28, 2021

(54) HUMAN FIBROBLAST GROWTH FACTOR-2 MUTANT WITH INCREASED STABILITY, AND USE THEREOF

(71) Applicant: PnP Biopharm Co., Ltd., Seoul (KR)

(72) Inventors: Hang-Cheol Shin, Seoul (KR); Jong-Kwang Oh, Seoul (KR)

(73) Assignee: PnP Biopharm Co., Ltd., Seoul (KR)

( * ) Notice: Subject to any disclaimer, the term of this patent is extended or adjusted under 35 U.S.C. 154(b) by 118 days.

(21) Appl. No.: 15/579,235

(22) PCT Filed: Jul. 24, 2015

(86) PCT No.: PCT/KR2015/007734
§ 371 (c)(1),
(2) Date: Dec. 4, 2017

(87) PCT Pub. No.: WO2016/195157
PCT Pub. Date: Dec. 8, 2016

(65) Prior Publication Data
US 2020/0188267 A1  Jun. 18, 2020

(30) Foreign Application Priority Data

Jun. 4, 2015 (KR) .................. 10-2015-0078930

(51) Int. Cl.
*C07K 14/50* (2006.01)
*A61K 8/64* (2006.01)
*A61Q 19/00* (2006.01)

(52) U.S. Cl.
CPC ............. *A61K 8/64* (2013.01); *A61Q 19/00* (2013.01); *C07K 14/50* (2013.01); *C07K 14/503* (2013.01)

(58) Field of Classification Search
None
See application file for complete search history.

(56) References Cited

U.S. PATENT DOCUMENTS 5,851,990 A * 12/1998 Fujishima ............... A61P 7/02
514/9.1
8,168,588 B2 * 5/2012 Williams ............ A61K 9/0019
514/7.6

FOREIGN PATENT DOCUMENTS

JP          05-262798        10/1993
WO     WO 2016/195157     * 12/2016

* cited by examiner

*Primary Examiner* — Marianne P Allen

(57) ABSTRACT

The present disclosure relates to a highly stable basic fibroblast growth factor mutant, and a use thereof. More specifically, the present disclosure provides: a highly stable basic fibroblast growth factor (bFGF) mutant, in which two or more amino acids in an amino acid sequence of SEQ ID NO: 1 are substituted with serine and one or more amino acids are substituted with cysteine; a DNA base sequence encoding the bFGF mutant; an expression vector including the DNA base sequence; a transformant transformed by the expression vector; a method of producing the bFGF mutant; and a composition including the bFGF mutant as an active ingredient. According to the present disclosure, the bFGF mutant of the present disclosure has excellent stability in an aqueous solution state and excellent thermal stability, and thus it is possible to produce functional cosmetics and skin inflammation medicines which do not lose activity, unlike conventional wild-type bFGF products, even during distribution and storage.

1 Claim, 13 Drawing Sheets
Specification includes a Sequence Listing.

SEQUENCE LISTING

<160> NUMBER OF SEQ ID NOS: 46

<210> SEQ ID NO 1
<211> LENGTH: 146
<212> TYPE: PRT
<213> ORGANISM: Homo sapiens

<400> SEQUENCE: 1

```
Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
        115                 120                 125

Lys Thr Gly Pro Gly Gln Lys Ala Ile Leu Phe Leu Pro Met Ser Ala
    130                 135                 140

Lys Ser
145
```

<210> SEQ ID NO 2
<211> LENGTH: 438
<212> TYPE: DNA
<213> ORGANISM: Homo sapiens

<400> SEQUENCE: 2

```
cccgccttgc ccgaggatgg cggcagcggc gccttcccgc ccggccactt caaggacccc      60
aagcggctgt actgcaaaaa cggggggcttc ttcctgcgca tccacccga cggccgagtt     120 gacggggtcc gggagaagag cgaccctcac atcaagctac aacttcaagc agaagagaga     180
ggagttgtgt ctatcaaagg agtgtgtgct aaccgttacc tggctatgaa ggaagatgga     240
agattactgg cttctaaatg tgttacggat gagtgttttct tttttgaacg attggaatct     300
aataactaca atacttaccg gtcaaggaaa tacaccagtt ggtatgtggc actgaagcga     360
actgggcagt ataaacttgg atccaaaaca ggacctgggc agaaagctat acttttttctt    420 ccaatgtctg ctaagagc                                                   438
```

<210> SEQ ID NO 3
<211> LENGTH: 28
<212> TYPE: DNA
<213> ORGANISM: Artificial Sequence
<220> FEATURE:
<223> OTHER INFORMATION: primer

<400> SEQUENCE: 3

```
ggcgggcata tgcccgcctt gcccgagg                                        28
```

<210> SEQ ID NO 4
<211> LENGTH: 33

<212> TYPE: DNA
<213> ORGANISM: Artificial Sequence
<220> FEATURE:
<223> OTHER INFORMATION: primer

<400> SEQUENCE: 4
tgatgaggat cctcatcagc tcttagcaga cat          33

<210> SEQ ID NO 5
<211> LENGTH: 33
<212> TYPE: DNA
<213> ORGANISM: Artificial Sequence
<220> FEATURE:
<223> OTHER INFORMATION: primer

<400> SEQUENCE: 5
tctatcaaag gagtgtctgc taaccgttac ctg          33

<210> SEQ ID NO 6
<211> LENGTH: 33
<212> TYPE: DNA
<213> ORGANISM: Artificial Sequence
<220> FEATURE:
<223> OTHER INFORMATION: primer

<400> SEQUENCE: 6
caggtaacgg ttagcagaca ctcctttgat aga          33

<210> SEQ ID NO 7
<211> LENGTH: 33
<212> TYPE: DNA
<213> ORGANISM: Artificial Sequence
<220> FEATURE:
<223> OTHER INFORMATION: primer

<400> SEQUENCE: 7
ttactggctt ctaaatctgt tacggatgag tgt          33

<210> SEQ ID NO 8
<211> LENGTH: 33
<212> TYPE: DNA
<213> ORGANISM: Artificial Sequence
<220> FEATURE:
<223> OTHER INFORMATION: primer

<400> SEQUENCE: 8
acactcatcc gtaacagatt tagaagccag taa          33

<210> SEQ ID NO 9
<211> LENGTH: 33
<212> TYPE: DNA
<213> ORGANISM: Artificial Sequence
<220> FEATURE:
<223> OTHER INFORMATION: primer

<400> SEQUENCE: 9
gctaaccgtt acctgtgcat gaaggaagat gga          33

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
tccatcttcc ttcatgcaca ggtaacggtt agc        33

<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11
aagcggctgt actgctgcaa cgggggcttc ttc        33

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
gaagaagccc ccgttgcagc agtacagccg ctt        33

<210> SEQ ID NO 13
<211> LENGTH: 33
<212> TYPE: DNA
<213> ORGANISM: Artificial Sequence
<220> FEATURE:
<223> OTHER INFORMATION: primer

<400> SEQUENCE: 13
ggcttcttcc tgcgctgcca ccccgacggc cga        33

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
tcggccgtcg gggtggcagc gcaggaagaa gcc        33

<210> SEQ ID NO 15
<211> LENGTH: 33
<212> TYPE: DNA
<213> ORGANISM: Artificial Sequence
<220> FEATURE:
<223> OTHER INFORMATION: primer

<400> SEQUENCE: 15
caccccgacg gccgatgcga cggggtccgg gag        33

<210> SEQ ID NO 16
<211> LENGTH: 33
<212> TYPE: DNA
<213> ORGANISM: Artificial Sequence
<220> FEATURE:
<223> OTHER INFORMATION: primer

<400> SEQUENCE: 16 ctccccggacc ccgtcgcatc ggccgtcggg gtg        33

<210> SEQ ID NO 17
<211> LENGTH: 33
<212> TYPE: DNA
<213> ORGANISM: Artificial Sequence

```
<220> FEATURE:
<223> OTHER INFORMATION: primer

<400> SEQUENCE: 17
gagaagagcg acccttgcat caagctacaa ctt                           33

<210> SEQ ID NO 18
<211> LENGTH: 33
<212> TYPE: DNA
<213> ORGANISM: Artificial Sequence
<220> FEATURE:
<223> OTHER INFORMATION: primer

<400> SEQUENCE: 18
aagttgtagc ttgatgcaag ggtcgctctt ctc                           33

<210> SEQ ID NO 19
<211> LENGTH: 33
<212> TYPE: DNA
<213> ORGANISM: Artificial Sequence
<220> FEATURE:
<223> OTHER INFORMATION: primer

<400> SEQUENCE: 19
agcgaccctc acatctgcct acaacttcaa gca                           33

<210> SEQ ID NO 20
<211> LENGTH: 33
<212> TYPE: DNA
<213> ORGANISM: Artificial Sequence
<220> FEATURE:
<223> OTHER INFORMATION: primer

<400> SEQUENCE: 20
tgcttgaagt tgtaggcaga tgtgagggtc gct                           33

<210> SEQ ID NO 21
<211> LENGTH: 33
<212> TYPE: DNA
<213> ORGANISM: Artificial Sequence
<220> FEATURE:
<223> OTHER INFORMATION: primer

<400> SEQUENCE: 21
aaccgttacc tggcttgcaa ggaagatgga aga                           33

<210> SEQ ID NO 22
<211> LENGTH: 33
<212> TYPE: DNA
<213> ORGANISM: Artificial Sequence
<220> FEATURE:
<223> OTHER INFORMATION: primer

<400> SEQUENCE: 22
tcttccatct tccttgcaag ccaggtaacg gtt                           33

<210> SEQ ID NO 23
<211> LENGTH: 33
<212> TYPE: DNA
<213> ORGANISM: Artificial Sequence
<220> FEATURE:
<223> OTHER INFORMATION: primer

<400> SEQUENCE: 23
accagttggt atgtgtgcct gaagcgaact ggg                           33
```

```
<210> SEQ ID NO 24
<211> LENGTH: 33
<212> TYPE: DNA
<213> ORGANISM: Artificial Sequence
<220> FEATURE:
<223> OTHER INFORMATION: primer

<400> SEQUENCE: 24
cccagttcgc ttcaggcaca cataccaact ggt                              33

<210> SEQ ID NO 25
<211> LENGTH: 33
<212> TYPE: DNA
<213> ORGANISM: Artificial Sequence
<220> FEATURE:
<223> OTHER INFORMATION: primer

<400> SEQUENCE: 25
gttgtgtcta tcaaatgcgt gtctgctaac cgt                              33

<210> SEQ ID NO 26
<211> LENGTH: 33
<212> TYPE: DNA
<213> ORGANISM: Artificial Sequence
<220> FEATURE:
<223> OTHER INFORMATION: primer

<400> SEQUENCE: 26
acggttagca gacacgcatt tgatagacac aac                              33

<210> SEQ ID NO 27
<211> LENGTH: 33
<212> TYPE: DNA
<213> ORGANISM: Artificial Sequence
<220> FEATURE:
<223> OTHER INFORMATION: primer

<400> SEQUENCE: 27
gtgtctatca aaggatgctc tgctaaccgt tac                              33

<210> SEQ ID NO 28
<211> LENGTH: 33
<212> TYPE: DNA
<213> ORGANISM: Artificial Sequence
<220> FEATURE:
<223> OTHER INFORMATION: primer

<400> SEQUENCE: 28
gtaacggtta gcagagcatc ctttgataga cac                              33

<210> SEQ ID NO 29
<211> LENGTH: 33
<212> TYPE: DNA
<213> ORGANISM: Artificial Sequence
<220> FEATURE:
<223> OTHER INFORMATION: primer

<400> SEQUENCE: 29
atcaaaggag tgtcttgcaa ccgttacctg gct                              33

<210> SEQ ID NO 30
<211> LENGTH: 33
<212> TYPE: DNA
<213> ORGANISM: Artificial Sequence
<220> FEATURE:
<223> OTHER INFORMATION: primer
```

-continued

```
<400> SEQUENCE: 30
agccaggtaa cggttgcaag acactccttt gat                                 33

<210> SEQ ID NO 31
<211> LENGTH: 33
<212> TYPE: DNA
<213> ORGANISM: Artificial Sequence
<220> FEATURE:
<223> OTHER INFORMATION: primer

<400> SEQUENCE: 31
aaggaagatg gaagatgcct ggcttctaaa tct                                 33

<210> SEQ ID NO 32
<211> LENGTH: 33
<212> TYPE: DNA
<213> ORGANISM: Artificial Sequence
<220> FEATURE:
<223> OTHER INFORMATION: primer

<400> SEQUENCE: 32
agatttagaa gccaggcatc ttccatcttc ctt                                 33

<210> SEQ ID NO 33
<211> LENGTH: 33
<212> TYPE: DNA
<213> ORGANISM: Artificial Sequence
<220> FEATURE:
<223> OTHER INFORMATION: primer

<400> SEQUENCE: 33
gatggaagat tactgtgctc taaatctgtt acg                                 33

<210> SEQ ID NO 34
<211> LENGTH: 33
<212> TYPE: DNA
<213> ORGANISM: Artificial Sequence
<220> FEATURE:
<223> OTHER INFORMATION: primer

<400> SEQUENCE: 34
cgtaacagat ttagagcaca gtaatcttcc atc                                 33

<210> SEQ ID NO 35
<211> LENGTH: 33
<212> TYPE: DNA
<213> ORGANISM: Artificial Sequence
<220> FEATURE:
<223> OTHER INFORMATION: primer

<400> SEQUENCE: 35
tacaatactt accggtgcag gaaatacacc agt                                 33

<210> SEQ ID NO 36
<211> LENGTH: 33
<212> TYPE: DNA
<213> ORGANISM: Artificial Sequence
<220> FEATURE:
<223> OTHER INFORMATION: primer

<400> SEQUENCE: 36
actggtgtat ttcctgcacc ggtaagtatt gta                                 33

<210> SEQ ID NO 37
```

<210> SEQ ID NO 37
<211> LENGTH: 33
<212> TYPE: DNA
<213> ORGANISM: Artificial Sequence
<220> FEATURE:
<223> OTHER INFORMATION: primer

<400> SEQUENCE: 37
ggacctgggc agaaatgcat acttttctt cca          33

<210> SEQ ID NO 38
<211> LENGTH: 33
<212> TYPE: DNA
<213> ORGANISM: Artificial Sequence
<220> FEATURE:
<223> OTHER INFORMATION: primer

<400> SEQUENCE: 38
tggaagaaaa agtatgcatt tctgcccagg tcc          33

<210> SEQ ID NO 39
<211> LENGTH: 33
<212> TYPE: DNA
<213> ORGANISM: Artificial Sequence
<220> FEATURE:
<223> OTHER INFORMATION: primer

<400> SEQUENCE: 39
cctgggcaga aagcttgcct ttttcttcca atg          33

<210> SEQ ID NO 40
<211> LENGTH: 33
<212> TYPE: DNA
<213> ORGANISM: Artificial Sequence
<220> FEATURE:
<223> OTHER INFORMATION: primer

<400> SEQUENCE: 40
cattggaaga aaaggcaag ctttctgccc agg          33

<210> SEQ ID NO 41
<211> LENGTH: 33
<212> TYPE: DNA
<213> ORGANISM: Artificial Sequence
<220> FEATURE:
<223> OTHER INFORMATION: primer

<400> SEQUENCE: 41
gggcagaaag ctatatgctt tcttccaatg tct          33

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
agacattgga agaaagcata tagctttctg ccc          33

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43

```
tttcttccaa tgtcttgcaa gagctgatga                                              30

<210> SEQ ID NO 44
<211> LENGTH: 30
<212> TYPE: DNA
<213> ORGANISM: Artificial Sequence
<220> FEATURE:
<223> OTHER INFORMATION: primer

<400> SEQUENCE: 44
tcatcagctc ttgcaagaca ttggaagaaa                                              30

<210> SEQ ID NO 45
<211> LENGTH: 33
<212> TYPE: DNA
<213> ORGANISM: Artificial Sequence
<220> FEATURE:
<223> OTHER INFORMATION: primer

<400> SEQUENCE: 45
gagaagagcg acccttatat caagctacaa ctt                                          33

<210> SEQ ID NO 46
<211> LENGTH: 33
<212> TYPE: DNA
<213> ORGANISM: Artificial Sequence
<220> FEATURE:
<223> OTHER INFORMATION: primer

<400> SEQUENCE: 46
aagttgtagc ttgatataag ggtcgctctt ctc                                          33
```

HUMAN FIBROBLAST GROWTH FACTOR-2 MUTANT WITH INCREASED STABILITY, AND USE THEREOF

TECHNICAL FIELD

The present disclosure relates to a highly stable basic fibroblast growth factor mutant and a use thereof.

REFERENCE TO AN ELECTRONIC SEQUENCE LISTING

The contents of the electronic sequence listing (OP16-0060HSUS_SEQLIST.txt; Size: 10,178 bytes; and Date of Creation: Jul. 26, 2020), filed via EFS-Web on Jul. 26, 2020, is herein incorporated by reference in its entirety.

BACKGROUND ART

Growth factors play an important role in regulating cell growth, proliferation, and differentiation. Therefore, there is a system that naturally repairs the damage and aging of the skin due to internal and external factors such as wound, surgery and the growth factors play an important role here. In order to maintain the function of each tissue, various growth factors are generated, maintains at a constant concentration, and performs a function. As the age increases, the concentration of growth factors decreases in each tissue such as skin, aging progresses, such as wrinkles are formed and the elasticity is weakened due to weakening of cell regeneration and division function.

Among them, bFGF (Basic Fibroblast Growth Factor, FGF-2) is composed of 154 amino acids and is composed of a polypeptide having a molecular weight of 17.123 Dalton. It plays an important role in development, angiogenesis and wound healing. FGF-2 is a potent mediator of wound healing, angiogenesis, and growth of the nervous system, as mitogen and chemotactic factor.

However, the growth factors present in these blood and tissues are known to have a very short body half-life of about several minutes. In particular, bFGF has four cysteine residues that do not form disulfide bonds in its structure, and thus there is a problem that the stability is greatly affected.

In addition, the bioavailability of protein therapeutic agents such as bFGF is often limited by short plasma half-lives and susceptibility to proteases, hindering maximum clinical efficacy. In order to develop the use of bFGF more effectively, physico-chemical stability in vitro as well as stability in vivo should be improved so that the use in the manufacture, storage and distribution of cosmetics such as quasi-drugs and creams will increase.

Thus, there is a need to develop new bFGF mutants that are more stable and active.

PRIOR PATENT DOCUMENT

Korean Patent Laid-Open Publication No. 1020090083062

DISCLOSURE

Technical Problem

The present inventors have made an effort to develop a highly stable basic fibroblast growth factor (bFGF) mutant. As a result, in order to increase the stability of bFGF protein and prevent dimerization, a molecular design method of giving a modification to the amino acid sequence of the protein was applied to obtain excellent effects in terms of thermal stability and stability in aqueous solution. The present disclosure has been completed by confirming the above.

Accordingly, an object of the present disclosure is to provide a highly stable basic fibroblast growth factor mutant.

It is another object of the present disclosure to provide a DNA base sequence encoding a bFGF mutant.

It is still another object of the present disclosure to provide an expression vector including the DNA base sequence.

It is still another object of the present disclosure to provide a transformant transformed by the expression vector.

It is still another object of the present disclosure to provide a method for producing a highly stable basic fibroblast growth factor mutant.

It is still another object of the present disclosure to provide a cosmetic composition for improving skin condition, in which the cosmetic composition includes a highly stable bFGF mutant as an active ingredient.

It is still another object of the present disclosure to provide a pharmaceutical composition for preventing or treating skin diseases, in which the pharmaceutical composition includes a highly stable bFGF mutant as an active ingredient.

Technical Solution

In order to accomplish the above objects, the present disclosure provides a highly stable bFGF mutant, in which two or more amino acids in the amino acid sequence of SEQ ID NO: 1 are substituted with serine, one or more amino acids are substituted with cysteine, and one amino acid of the surface is substituted with tyrosine.

The term "basic fibroblast growth factor (bFGF)" or "FGF-2" as used herein refers to a basic protein with a molecular weight of about 18 KDa (pI 9.58), which is mainly secreted in the pituitary gland and promotes the growth of various mesoderm-derived cells. In addition, it is a protein that promotes the growth of endothelial cells and smooth muscle cells, and exhibits excellent effects in trauma treatment and vasculogenesis. It is known to increase the synthesis of collagen and elastin, thereby maintaining skin elasticity, helping normal cell growth, promoting recovery from wounds and performing the healing action.

The mutant of the present disclosure can be prepared by selecting a site which is not related to the active site of bFGF through a method of homology alignment between a tertiary structure and a species of the bFGF and a protein molecule modeling using a computer, and through mutant experiments. The cysteine amino acid residue forming a disulfide bond with bFGF and another bFGF is substituted with a serine residue having a similar structure, thereby increasing stability against precipitation due to surface disulfide bonds. In addition, the stability is improved by a method of reducing loop entropy by additionally producing a disulfide bond by substituting one residue near the loop in bFGF with cysteine. In addition, the stability is improved by a method of substituting Tyr for His residue in bFGF to increase the hydrogen bond and Van der walls interaction, thereby stabilizing the protein cavity structure.

According to a preferred embodiment of the present disclosure, the amino acid substituted with the serine is the 69th cysteine and the 87th cysteine in the amino acid sequence of SEQ ID NO: 1.

According to a preferred embodiment of the present disclosure, the amino acid substituted with the cysteine is at least one selected from the group consisting of the 26th lysine in the amino acid sequence of SEQ ID NO: 1; the 34th isoleucine in the amino acid sequence of SEQ ID NO: 1; the 40th valine in the amino acid sequence of SEQ ID NO: 1; the 50th histidine in the amino acid sequence of SEQ ID NO: 1; the 52nd lysine in the amino acid sequence of SEQ ID NO: 1; the 75th alanine in the amino acid sequence of SEQ ID NO: 1; the 76th methionine in the amino acid sequence of SEQ ID NO: 1; the 117th alanine in the amino acid sequence of SEQ ID NO: 1; the 67th glycine in the amino acid sequence of SEQ ID NO: 1; the 68th valine in the amino acid sequence of SEQ ID NO: 1; the 70th alanine in the amino acid sequence of SEQ ID NO: 1; the 82nd leucine in the amino acid sequence of SEQ ID NO: 1; the 84th alanine in the amino acid sequence of SEQ ID NO: 1; the 108th serine in the amino acid sequence of SEQ ID NO: 1; the 136th alanine in the amino acid sequence of SEQ ID NO: 1; the 137th isoleucine in the amino acid sequence of SEQ ID NO: 1; the 138th leucine in the amino acid sequence of SEQ ID NO: 1; and 144th alanine in the amino acid sequence of SEQ ID NO: 1, more preferably at least one selected from the group consisting of the 40th valine in the amino acid sequence of SEQ ID NO: 1; the 50th histidine in the amino acid sequence of SEQ ID NO: 1; the 52nd lysine in the amino acid sequence of SEQ ID NO: 1; the 75th alanine in the amino acid sequence of SEQ ID NO: 1; the 76th methionine in the amino acid sequence of SEQ ID NO: 1; and the 117th alanine in the amino acid sequence of SEQ ID NO: 1, and most preferably the 75th alanine in the amino acid sequence of SEQ ID NO: 1.

As a further mutant, a mutant obtained by substituting, with tyrosine, histidine $50^{th}$ residue, which is a residue exposed on the surface of a protein, in a mutant in which the 75th alanine is substituted with cysteine is the most preferable mutant.

That is, the bFGF mutant of the present disclosure is a bFGF mutant in which the cysteine, which is the 69th and 87th amino acid residues of the wild-type human bFGF amino acid sequence (SEQ ID NO: 1), is all substituted with serine, substituted with tyrosine at the 50th histidine, the alanine, which is the 75th amino acid residue, is further substituted with cysteine to form disulfide bonds in the molecule, and the remaining amino acid sequence provides the same human bFGF mutein as the wild-type amino acid sequence.

The bFGF mutant of the present disclosure increases the stability against heat compared to the wild-type while maintaining the protein activity. As shown in the following Experimental Examples 1 to 3, the bFGF mutant has the activity equivalent to that of the wild-type, and the stability against heat is also remarkably increased. In the bFGF mutant, K75 (Stable basic Fibroblast Growth Factor, sbFGF) of the present disclosure, in which the $69^{th}$ and $87^{th}$ amino acids were substituted with serine and the $75^{th}$ amino acid was substituted with cysteine and the disulfide bond was induced, has improved the thermal stability superior to that of a control group, which is the wild-type bFGF, a bFGF mutant in which the $69^{th}$ and $87^{th}$ amino acids are substituted with serine and a bFGF mutant in which the $75^{th}$ amino acid is substituted with cysteine. In addition, in the case of HsbFGF substituted with tyrosine of the 50th histidine of K75, the thermal stability has improved as compared to the wild-type and K75, which are control groups.

According to another aspect of the present disclosure, there is provided a DNA base sequence (SEQ ID NO: 2) encoding the bFGF mutant and an expression vector including the same.

The expression vector of the present disclosure can be prepared by inserting the gene of bFGF into a general expression vector. In the preferred embodiment of the present disclosure, the pET21a vector is used as an expression vector, but not always limited thereto, and any cell expression vector generally used can be used. In a preferred embodiment of the present disclosure, a vector in which a bFGF gene is inserted into a pET21a vector was prepared and named "pSSB-bFGF" (illustrated in FIG. 1b).

According to another aspect of the present disclosure, there is provided a transformant which is a host cell transformed with the expression vector.

The bFGF mutant of the present disclosure can be prepared by a method of expressing a bFGF mutant by transforming a host cell with a vector including a gene encoding a bFGF mutant prepared by a site-specific mutagenesis method or the like.

The DNA encoding the bFGF mutant is a DNA encoding the amino acid of the substituted site of wild-type bFGF. Preferred DNA sequences encoding bFGF mutants are those in which the 69th and 87th codons are substituted with codons encoding serine and the 75th codon is substituted with the codons encoding cysteine. In addition, in the case of HsbFGF substituted with tyrosine of the $50^{th}$ histidine of K75, the thermal stability has improved as compared to the wild-type and K75, which are control groups.

On the other hand, it is well known that a nucleotide sequence of a DNA encoding the same amino acid sequence may be different because a plurality of codons encoding one amino acid is present due to degeneracy of the codon.

The DNA encoding the bFGF mutant may be chemically synthesized, or may be prepared by preparing a wild-type bFGF cDNA and using site-specific mutagenesis method based thereon.

The prepared DNA encoding the bFGF mutant of the present disclosure can be expressed using any suitable prokaryotic or eukaryotic expression systems well known in the pertinent art (Sambrook et al., Molecular Cloning, A Laboratory Manual, 2nd ed., Cold Spring Habor Laboratory, Cold Spring Harbor Laboratory Press, USA, 1989).

Expression is preferably performed in *E. coli* such as *Escherichia coli* BL21 (DE3), *Escherichia coli* JM109 (DE3), *Escherichia coli* NM522 and the like for non-glycosylated bFGF mutants, and suitable vectors that can be used for expression in *E. coli* are mentioned in the documents such as Sambrook, etc. (same as above), and theses such as Fiers, etc. ("Proced. 8th Int. Biotechnology Symposium", Soc. Frac, de Microbiol., Paris, (Durand et al., eds.), pp. 680-697, 1988).

Transformation of host cells by the vectors described above can be carried out by any of the conventional methods (Sambrook et al., Molecular Cloning, A Laboratory Manual, 1989; Ito et al., J. Bacteriol. 153:263, 1983).

When transforming *Escherichia coli*, a competent cell capable of absorbing DNA may be prepared, followed by treatment according to a known method or the like.

According to another aspect of the present disclosure, there is provided a method of producing a highly stable basic fibroblast growth factor (bFGF) mutant including the following steps of:

(a) culturing the transformant; and (b) isolating the mutant from the culture solution obtained in the step (a).

According to a preferred embodiment of the present disclosure, step (b) includes the steps of:

(c) cell-disrupting the transformant and isolating aggregates;

(d) removing the isolated aggregates;

(e) isolating and purifying the supernatant from which the aggregates have been removed by ion exchange resin chromatography; and (f) isolating and purifying the highly stable basic fibroblast growth factor mutant after the ion exchange resin using heparin affinity chromatography.

In general, host microorganisms including the target expression vector are cultured under their optimal growth conditions to the extent that they maximize production of the desired protein. For example, *Escherichia coli* BL21 (DE3) cells transformed with a vector including the ampicillin resistance gene as a selection marker are cultured at 37° C. in LB medium including ampicillin.

Recovery and purification of the produced bFGF mutant after culturing the transformed host cells can be carried out by various methods known in the pertinent art or by using them in combination. For example, bFGF mutants expressed in transformed *E. coli* cells can be recovered from the cell culture or after disruption of the cells by suitable methods known to the proteomics system.

Preferably, in order to purify the bFGF mutant, the culture solution of the recombinant *E. coli* cells is centrifuged to harvest the cells, and the harvested cells are suspended in a buffer solution to which lysozyme is added and ultrasonicated. The cell lysate is centrifuged to isolate the insoluble granular aggregates, and the isolated aggregates are removed. The supernatant liquid from which the aggregates have been removed is isolated and purified using ion exchange resin chromatography, and the ion-exchange resin is then isolated and purified using heparin affinity chromatography to obtain the resultant highly stable bFGF mutant.

According to another aspect of the present disclosure, there is provided a pharmaceutical composition for preventing or treating a skin disease including the above-mentioned highly stable bFGF mutant as an active ingredient.

As demonstrated in the following examples, the highly stable bFGF mutants of the present disclosure have the same activity as wild-type bFGF, have excellent thermal stability and stability in aqueous solution. Therefore, the composition of the present disclosure is very effective for preventing or treating skin diseases.

Preferably, the compositions of the present disclosure are used for the prevention or treatment of skin diseases such as skin inflammation, acute and chronic eczema, contact dermatitis, atopic dermatitis, seborrheic dermatitis, chronic simplex chronicus, intertrigo, deprivation dermatitis, papular urticaria, psoriasis, sunlight dermatitis, and acne.

In addition, the composition of the present disclosure can provide a composition for treating wound.

Preferably, the composition of the present disclosure is used for the treatment of closed wounds and open wounds. Examples of closure wounds include contusion or Burise and examples of open wounds include abrasion, laceration, avulsion, penetrated wound and gun shot wound.

The composition of the present disclosure is a pharmaceutical composition including (a) a pharmaceutically effective amount of the above-described bFGF mutant of the present disclosure; and (b) a pharmaceutically acceptable carrier.

As used herein, the term "pharmaceutically effective amount" means an amount sufficient to achieve efficacy or activity of the bFGF mutants described above.

The pharmaceutically acceptable carrier to be included in the pharmaceutical composition of the present disclosure is one usually used in the preparation, and includes lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate and mineral oil, etc., but is not limited thereto. The pharmaceutical composition of the present disclosure may further include a lubricant, a wetting agent, a sweetening agent, a flavoring agent, an emulsifying agent, a suspending agent, a preservative, etc., in addition to the above components. Suitable pharmaceutically acceptable carriers and preparations are described in detail in Remington's Pharmaceutical Sciences (19th ed., 1995).

The pharmaceutical composition of the present disclosure may be administered orally or parenterally, preferably parenterally. In the case of parenteral administration, the pharmaceutical composition may be administered by intravenous infusion, subcutaneous infusion, muscle infusion, intraperitoneal infusion, local administration, transdermal administration, etc.

A suitable dosage of the pharmaceutical composition of the present disclosure may vary depending on factors such as a preparation method, administration method, age, body weight, sex, pathological condition of a patient, food, administration time, administration route, excretion speed, reaction susceptibility. On the other hand, the preferred daily dosage of the pharmaceutical composition of the present disclosure is 0.001 to 100 mg/kg.

The pharmaceutical composition of the present disclosure may be prepared into a unit dosage form by formulating it using a pharmaceutically acceptable carrier and/or excipient according to a method which can be easily carried out by those having ordinary skill in the art to which the present disclosure belongs, or by intrusion into a multi-dose container. The formulations may be in the form of solutions, suspensions or emulsions in oils or aqueous media, or in the form of extracts, powders, granules, tablets, capsules or gels (e.g., hydrogels), and may additionally include dispersing or stabilizing agents.

According to another aspect of the present disclosure, there is provided a cosmetic composition for improving skin condition including the above-mentioned highly stable bFGF mutant as an active ingredient.

As demonstrated in the following examples, the highly stable bFGF mutants of the present disclosure have the same activity as wild-type bFGF, have excellent thermal stability and stability in aqueous solution. Therefore, the composition of the present disclosure is very effective for improving the skin condition.

Preferably, the composition of the present disclosure is used for improving the skin condition such as wrinkle improvement, skin elasticity improvement, skin aging prevention, hair loss prevention or hair growth promotion, skin moisturization improvement, black spot removal or acne treatment.

The composition of the present disclosure is a cosmetic composition including (a) a cosmetically effective amount of the above-described bFGF mutant of the present disclosure; and (b) a cosmetically acceptable carrier.

The term "cosmetically effective amount" as used herein means an amount sufficient to achieve the skin-improving effect of the composition of the present disclosure described above.

The cosmetic composition of the present disclosure may be prepared in any formulation conventionally produced in the art and may be formulated in the form of solutions, suspensions, emulsions, pastes, gels, creams, lotions, powders, soaps, surfactant-containing cleansing, oils, powder foundations, emulsion foundations, wax foundations and sprays, but is not limited thereto. More specifically, it can be prepared in the formulation of a soft lotion, a nutritional lotion, a nutritional cream, a massage cream, an essence, an eye cream, a cleansing cream, a cleansing foam, a cleansing water, a pack, a spray or a powder.

When the formulation of the present disclosure is a paste, cream or gel, an animal oil, vegetable oil, wax, paraffin, starch, tracant, cellulose derivative, polyethylene glycol, silicone, bentonite, silica, talc or zinc oxide may be used as a carrier ingredient.

In the case where the formulation of the present disclosure is a powder or a spray, lactose, talc, silica, aluminum hydroxide, calcium silicate or polyamide powder may be used as a carrier ingredient. In particular, in the case of a spray, a propellant such as a chlorofluorohydrocarbon, propane/butane or dimethyl ether may be included.

When the formulation of the present disclosure is a solution or an emulsion, a solvent, a solubilizer or an emulsifying agent is used as a carrier ingredient, and examples thereof include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol or sorbitan fatty acid esters.

When the formulation of the present disclosure is a suspension, a carrier ingredient such as water, a liquid diluent such as ethanol or propylene glycol, a suspension such as ethoxylated isostearyl alcohol, polyoxyethylene sorbitol ester and polyoxyethylene sorbitan ester, microcrystalline cellulose, aluminum metahydroxide, bentonite, agar or tracant, etc. may be used.

When the formulation of the present disclosure is a surfactant-containing cleansing, as the carrier ingredient, aliphatic alcohol sulfate, aliphatic alcohol ether sulfate, sulfosuccinic acid monoester, isethionate, imidazolinium derivative, methyltaurate, sarcosinate, fatty acid amide ether sulfates, alkylamidobetaines, aliphatic alcohols, fatty acid glycerides, fatty acid diethanolamides, vegetable oils, lanolin derivatives, or ethoxylated glycerol fatty acid esters, etc. may be used.

The ingredients included in the cosmetic composition of the present disclosure include, in addition to the bFGF mutant and the carrier ingredient as the active ingredient, ingredients commonly used in cosmetic compositions, and as an example, include conventional ingredients such as antioxidants, stabilizers, solubilizers, vitamins, pigments, and spices.

Since the compositions of the present disclosure include the above-described highly stable bFGF mutant of the present disclosure as an active ingredient, the description common to both of them is omitted in order to avoid the excessive complexity of the present specification.

Effect

According to the present disclosure, the bFGF mutant of the present disclosure has excellent stability in an aqueous solution state and excellent thermal stability, and thus it is possible to produce functional cosmetics which do not lose activity, unlike conventional wild-type bFGF products, even during distribution and storage, and can be used as a coating material for skin wound.

BEST MODE

Hereinafter, it will be apparent to a person having ordinary skill in the technical field to which the present disclosure pertains that the examples are for illustrative purposes only in more details and that the scope of the present disclosure is not construed as being limited by these examples without departing from gist of the present disclosure.

Figure 1:
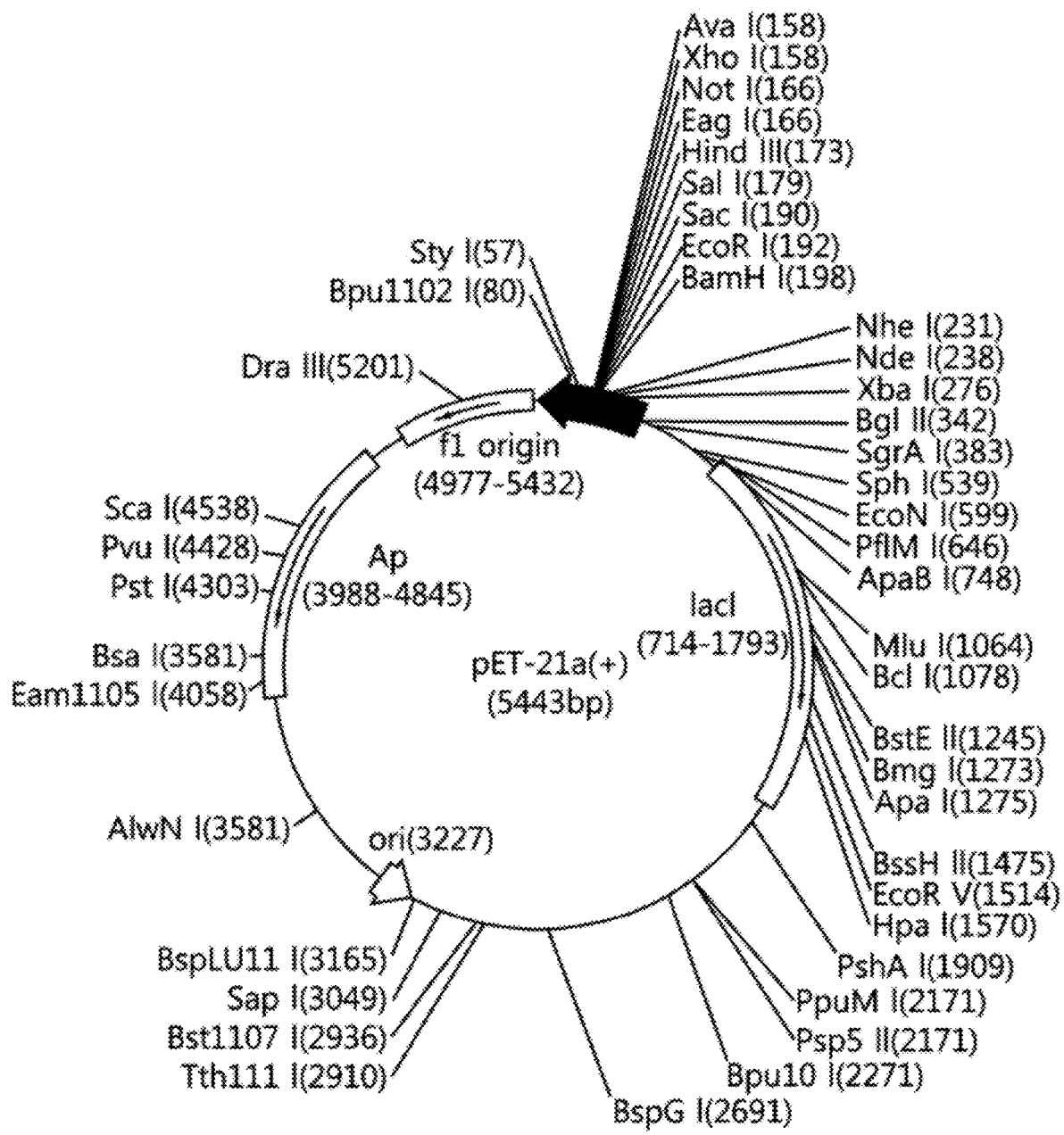
FIGS. 1 and 2 illustrate an overview of an assembly of the plasmid and pSSB-bFGF.

Experimental Methods and Materials
DNA Construction
The protein expression vector pET21a (FIG. 1) and *E. coli* expressing strain BL21 (DE3) and Rosetta (DE3) were purchased from Novagen and Top10 was used for the *E. coli* strain for cloning. All of the restriction enzymes used in the gene recombination were NEB (New England Biolabs) products, and the ligase was T4 DNA ligase of Roche. Ex taq DNA polymerase used in PCR is a product of Takara, and pfuUltra™ HF DNA polymerase used in point mutation is a product of Agilent. The DNA gel extraction kit and the plasmid mini prep kit are products of Cosmogenetech Inc. In addition, the primers were prepared by Cosmogenetech Inc. DNA sequencing was also performed by Cosmogenetech Inc.

Protein Expression

The expression vector IPTG (isopropyl-1-thio-β-D-galactopyranoside) and antibiotics ampicillin and chloramphenicol were both purchased from Sigma. Bacto tryptone and yeast extract used in the preparation of E. coli culture LB medium were purchased from BD (Becton Dicknson), and NaCl was purchased from Duksan.

Protein Purification

The reagents used in the purification process are as high in purity as possible, and the reagents used in the purification process are as follows. sodium phosphate monobasic (Sigma), sodium phosphate dibasic (Sigma), and sodium chloride (Sigma). Columns used in FPLC were GE healthcare's SP-sephrose, heparin affinity column.

FPLC

FPLC used GE UPC-800.

CD (Circular Dichroism)

The J-810 spectropolarimeter from Jasco was used for the CD.

Homology Modeling

Homology modeling used Modeller (Andrej Sali lab).

Energy Minimization

Energy minimization used Amber 99FF force filed included in Chimera.

Disulfide Prediction

YASARA Web server was used to predict the disulfide bond formation.

Disulfide Bond Distance Measurement

As a plotting program that measures the distance that enables disulfide bonds, protein contact map visualization (Andreas Viklund.) was used.

Structure of Protein

4FGF and 1BLA 1BLD registered in the PDB were used.

Vector System pET21a vector (Novagen) was used as an expression vector for producing mutant bFGF. The wild-type bFGF gene was obtained from PnP biopharm Co., Ltd., and the wild-type was amplified by PCR (polymerase chain reaction) using the following primers. The PCR products thus obtained were treated with Nde I and Xho I restriction enzymes and inserted into pET21a vector, and then bonded.

Point Mutation

In order to increase the stability of bFGF, the amino acid portion to be changed through the structure of the protein (PDB: 4FGF) and the molecular model method was found, and a Quikchange mutagenesis method using pfu Ultra™ DNA polymerase using the following primer (following Example 4) was used for amplification. To remove the wild-type bFGF template used, Dpn I reaction was performed to transform Top10, and mutants were identified by sequencing.

Expression of Wild-Type and Mutant bFGF

The bFGF-inserted recombinant vector was transformed into E. coli BL21 (DE3) by Heat shock method. The E. coli strain was inoculated into 500 ml LB medium containing 50 μg/ml ampicillin and grown at 37° C. until the O.D600 value reached 0.6. Then, 0.5 mM IPTG (isopropyl-1-thio-β-D-galactopyranoside) was added and cultured for 4 hours. When O. D600 value was 2.0 or more, cells were centrifuged at 8000 rpm for 10 minutes.

Cell Disruption

Cells were disrupted to obtain proteins in E. coli expressing bFGF protein. The harvest cells were suspended in 20 mM sodium phosphate buffer (pH 7.0) and disrupted with a sonicator at 4° C. Thereafter, the insoluble material (inclusion body) was removed by centrifugation at 13000 rpm for 15 minutes at 4° C., and the supernatant was selected and confirmed by SDS-PAGE.

Purification of Transformants

The cell solution disrupted by sonication was centrifuged at 13000 rpm for 15 minutes at 4° C. The supernatant was harvested, filtered through a 0.45 μm filter, and purified by FPLC (Fast Performance Liquid chromatography) SP column and Heparin column. The purification conditions were as follows: 100 mM NaCl solution A in 20 mM sodium phosphate (pH 7.0) buffer solution and 1M NaCl B in 20 mM sodium phosphate (pH 7.0) buffer solution were spilled to elute in a linear gradient from 0% A to 100% B at a rate of 2 ml/min in an SP column, and the fractions including the bFGF protein of about 18 KDa size were collected. Then, 500 mM NaCl solution A in 20 mM sodium phosphate (pH 7.0) buffer solution and 2M NaCl B in 20 mM sodium phosphate (pH 7.0) buffer solution were spilled to elute in a linear gradient from 0% A to 100% B at a rate of 2 ml/min in a heparin affinity column, and the fractions including the bFGF protein of about 18 KDa size were collected. At this time, fractions including bFGF were confirmed by SDS-PAGE analysis and then the quantification was performed.

Molecular Modeling

A candidate disulfide bondable group was set using 1BLA (NMR), which is a structure of proteins registered in the PDB. By using a protein contact map visualization program, the residues with C-alpha carbon distance of two amino acids of 7 Å or less and C-beta carbon distance of 5 Å were analyzed by using plot. Then, the formation of disulfide bonds were analyzed using a Yasara energy minimization server and performed energy minimization using AMBER force filed FF99 of chimera. Thereafter, the structure of the prepared protein was aligned with the wild-type bFGF to use the structure having the RMSD measurement value of 0.5 or less for experiments.

CD (Circular Dichroism)

For the structural analysis and TM measurement of wild-type bFGF and mutants, bFGF was dissolved in 20 mM sodium phosphate (pH 7.0), and the final concentration was adjusted constant to 0.2 mg/ml. In addition, it was put in a 0.1 cm cell, and the structure was analyzed under the conditions of the band width 1 nm in a 190 nm to 250 nm region, response 0.25 sec, data pitch 0.1 nm, scanning speed 20 nm/min, cell length 1 cm, accumulation 8 times, and temperature 20° C. In order to analyze the temperature stability, the melting temperature was performed at a 205 nm wavelength at 20° C. and 95° C. in 0.1 cm cell and 0.2 mg/ml concentration. Conditions were measured at 20° C. to 95° C. under the condition of 1° C./min.

Residue numbers and predicted results for disulfide bond are exhibited in Table 1.

TABLE 1

| | Disulfide prediction | Disulfide (alpha carbon) | Disulfide (beta carbon) | RMSD |
| --- | --- | --- | --- | --- |
| 34-67 | ◯ | 4.6 | 3.9 | 0.397 |
| 34-70 | ◯ | 6.5 | 4.7 | 0.414 |

TABLE 1-continued

| | Disulfide prediction | Disulfide (alpha carbon) | Disulfide (beta carbon) | RMSD |
|---|---|---|---|---|
| 34-84 | O | 6.7 | 4.6 | 0.353 |
| 40-82 | O | 6.2 | 4.3 | 0.38 |
| 50-69 | X | 5.7 | 4.9 | 0.385 |
| 52-68 | X | 6 | 4.6 | 0.367 |
| 75-92 | O | 4.9 | 3.9 | 0.395 |
| 76-108 | O | 6.2 | 4.9 | 0.403 |
| 117-136 | X | 5.1 | 3.9 | 0.386 |
| 117-137 | O | 4.5 | 4.5 | 0.403 |

Cell Proliferation Assay

In order to confirm whether the produced wild-type bFGF and the mutant actually exhibit activity, an experiment using cell proliferation ability was carried out by Genewel Inc. NIH-3T3 cells used for the experiment were maintained in a DMEM complete medium including 10% heat-inactivated fetal bovine serum, 100 units/ml penicillin, and 100 mg/ml streptomycin. $2 \times 10^3$ cells/well of NIH-3T3 cells were seeded in a 96 well culture plate. 24-hour cultured NIH-3T3 cells were starvated in a serum-free DMEM medium and then treated with the sample solution in DMEM medium including 0.5% FBS per concentration, and cultured for 72 hours. After culturing, 10 μl of MTT[3-(4,5-dimethylthiazol-2-yl)-2,5-diphenyl-2H-tetrazolium bromide] solution was added and reacted for 2 hours. Formazan crystal was dissolved with 100 μl of DMSO. Absorbance was measured at a wavelength of 540 nm using a spectrophotometer. The susceptibility to the drug was compared by the percentage of the absorbance of the drug untreated well (control) in the drug treated wells.

Incubation Test

Incubation tests of wild-type bFGF and mutants were performed to confirm the storage at room temperature. Each wild-type FGF-2 and mutants were dissolved at 0.5 mg/ml in 1×PBS (pH 7.3) and incubated at 37° C., 50° C. and 60° C. water baths. They were sampled in the unit of 24 hours, and then centrifuged at 13000 rpm for 15 minutes at 4° C. to obtain only a supernatant. Through nano drop, the quantification and HPLC analysis were performed.

Example 1: Construction of pSSB-bFGF Plasmid Including Human bFGF cDNA

DNA encoding bFGF was prepared by polymerase chain reaction using a human mononuclear cell cDNA library as a template and a primer. The base sequence of the primers used is as follows:

```
Sense primer
                                          (SEQ ID NO: 3)
5'-GGCGGGCATATGCCCGCCTTGCCCGAGG-3'
and antisense primer
                                          (SEQ ID NO: 4)
3'-TGATGAGGATCCTCATCAGCTCTTAGCAGACAT-5'.
```

Figure 2:
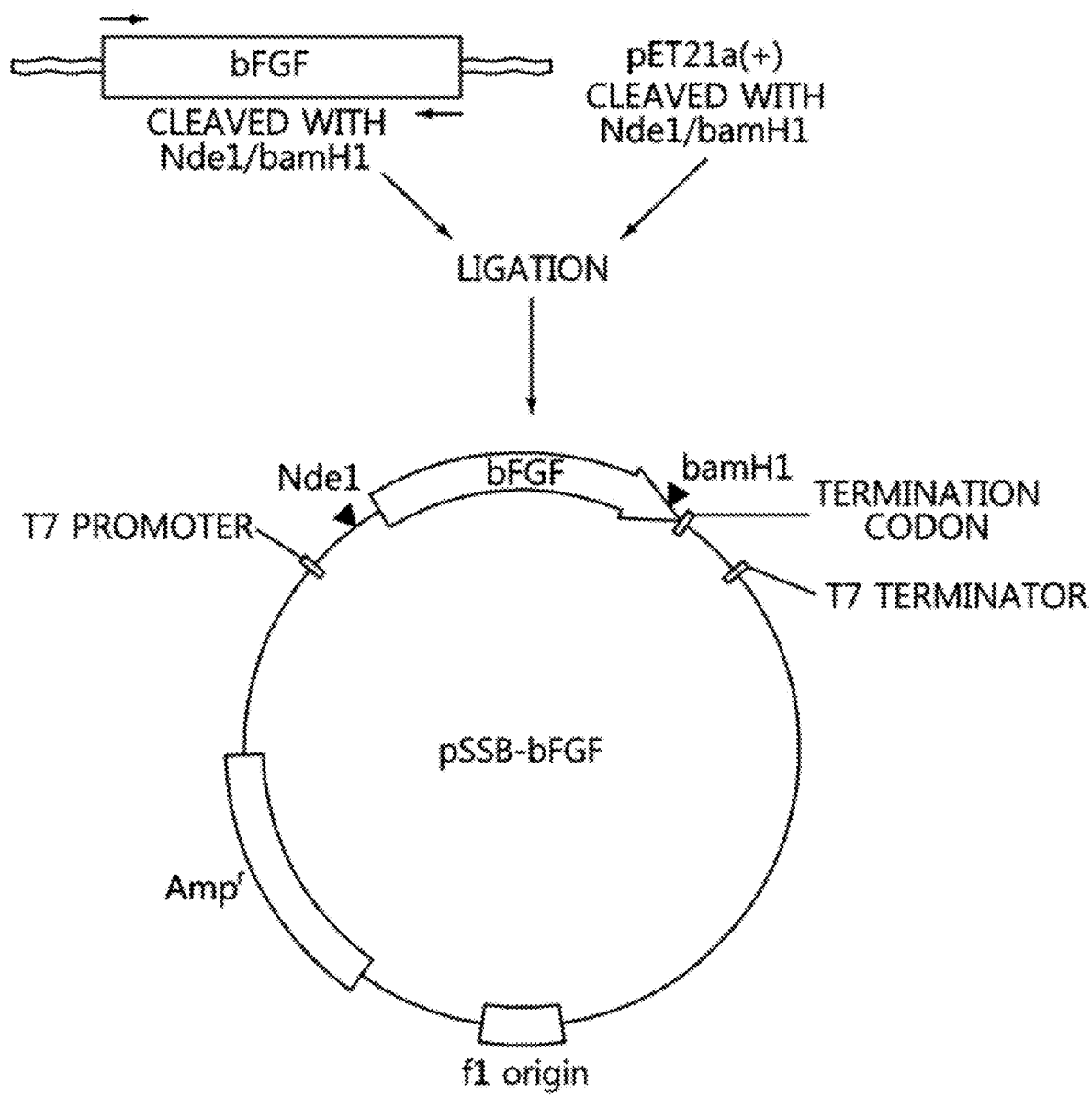
Figure 3:
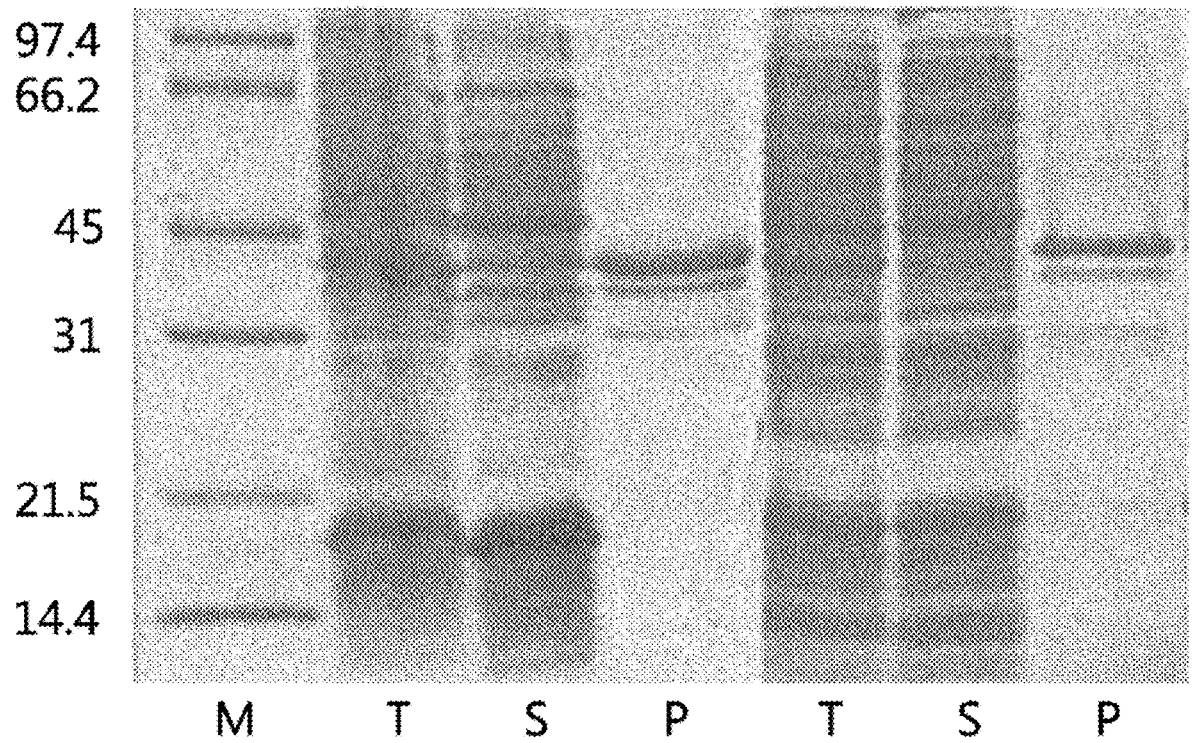
FIGS. 3 and 4 illustrate SDS-PAGE results of wild-type bFGF and the bFGF mutant of the present disclosure of T (suspension after cell disruption) S (supernatant after cell disruption) P (insoluble aggregate after cell disruption) after cell disruption.
Figure 4:
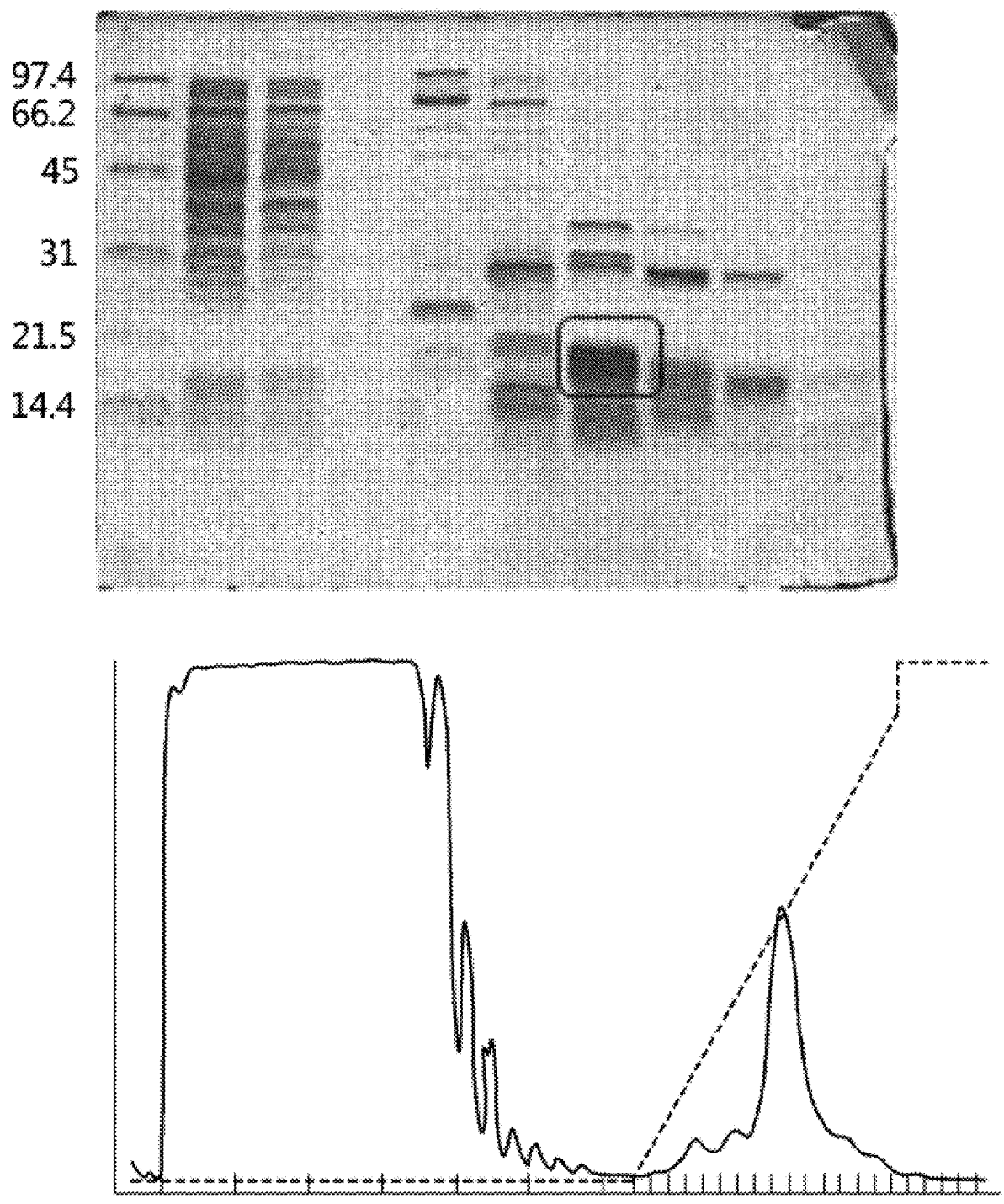

The bFGF portion of FIG. 2 was amplified using the primers described above. 1 μg of the amplified DNA fragment was dissolved in 50 μl of TE (pH 8.0) solution, and then 2 units of Nde I (NEB) and 2 units of Bam HI (NEB) were mixed, and reacted at 37° C. for 2 hours to have a Nde I restriction enzyme site at the 5'-terminus and a Bam HI restriction enzyme site at the 3'-terminus. After purifying only DNA using a DNA purification kit (GeneAll), 20 ng of this DNA fragment was treated with Nde I and Bam HI in the same manner, and the prepared 20 ng of the pET21a(+) plasmid (Novagen) was mixed with 10 μl of TE (pH 8.0) solution, followed by addition of 1 unit of T4 DNA ligase (NEB), followed by reaction at 16° C. for 4 hours and bonding. The plasmid thus prepared was named pSSB-bFGF.

Example 2: Preparation of *Escherichia coli* Transformants of Human bFGF

Expression plasmid pSSB-bFGF was transformed into *E. coli* BL21 (DE3) by heat shock. Colonies resistant to ampicillin, generated in the solid medium after transformation, were selected and inoculated into 10 ml of LB medium (LB/ampicillin). After culturing for 12 hours at 37° C., it was mixed with 100% glycerol in a ratio of 1:1 and a stock was stored at −70° C.

Example 3: Purification of Human bFGF

The stock prepared in Example 2 was inoculated into 10 ml of LB medium (LB/ampicillin) and cultured for 12 hours or longer. Then, the cells were transferred to 500 ml of LB medium (LB/ampicillin) and IPTG (isopropyl-1-thio-β-D-galactopyranoside) was added so that a final concentration became 0.5 mM at an absorbance of O.D 0.4 to 0.5 at 600 nm. The cells were shaking cultured at 200 rpm for 4 hours at 37° C., and then centrifuged at 8000 rpm for 10 minutes to obtain *E. coli* pellets. The pellet was suspended in 25 ml of 20 mM sodium phosphate (pH 7.0) buffer solution, and the cells were disrupted by an ultrasonication method.

The cell lysate disrupted by a ultrasonication method was centrifuged at 13000 rpm for 15 minutes at 4° C. The supernatant was collected and filtered using a 0.45 μm filter. The solution was purified by FPLC (Fast Performance Liquid chromatography), SP column and Heparin column. The conditions for purification were as follows: 100 mM NaCl solution A in 20 mM sodium phosphate (pH 7.0) buffer solution and 2 M NaCl B in 20 mM sodium phosphate (pH 7.0) buffer solution were spilled to elute in a linear gradient from 0% A to 50% B at a rate of 2 ml/min in an SP column, and the fractions including the bFGF protein of about 18 KDa size were collected. Then, 100 mM NaCl solution A in 20 mM sodium phosphate (pH 7.0) buffer solution and 2M NaCl B in 20 mM sodium phosphate (pH 7.0) buffer solution were spilled to elute in a linear gradient from 50% A to 100% B at a rate of 2 ml/min in an SP column, and the fractions including the bFGF protein of about 18 KDa size were collected. At this time, fractions including bFGF were confirmed by SDS-PAGE analysis and then the quantification was performed to obtain 10 mg of bFGF.

Example 4: Construction of pSSB-bFGF Mutant Plasmid pSSB-bFGF mutant plasmids were prepared by PCR using pfuUltraTMHF DNA polymerase as the template for the wild-type pSSB-bFGF plasmid and two complementary primers corresponding to the respective mutants. Then, the wild-type pSSB-bFGF plasmid, which was a template, was digested with Dpn I and transformed into *E. coli* Top10 by heat shock. Colonies resistant to ampicillin generated in the solid medium after transformation were selected and inoculated into 10 ml of LB medium (LB/ampicillin). After culturing for 16 hours at 37° C., DNA prep was performed and sequencing of the DNA obtained by DNA prep confirmed pSSB-bFGF mutant plasmids. The base sequence of the primers used is provided as follows:

sense primer 5'-TCT ATC AAA GGA GTG TCT GCT AAC CGT TAC CTG-3' (SEQ ID NO: 5) and the antisense primer 3'-CAG GTA ACG GTT AGC AGA CAC TCC TTT GAT AGA-5' (SEQ ID NO: 6) at the substitution of the 69th cysteine codon TGT with serine codon TCT;

sense primer 5'-TTA CTG GCT TCT AAA TCT GTT ACG GAT GAG TGT-3' (SEQ ID NO: 7) and the antisense primer 3'-ACA CTC ATC CGT AAC AGA TTT AGA AGC CAG TAA-5' (SEQ ID NO: 8) at the substitution of the 89th cysteine codon TGT with serine codon TCT;

sense primer 5'-GCT AAC CGT TAC CTG TGC ATG AAG GAA GAT GGA-3' (SEQ ID NO: 9) and the antisense primer 3'-TCC ATC TTC CTT CAT GCA CAG GTA ACG GTT AGC-5' (SEQ ID NO: 10) at the substitution of the 75th alanine codon GCT with serine codon TCT;

sense primer 5'-AAG CGG CTG TAC TGC TGC AAC GGG GGC TTC TTC-3' (SEQ ID NO: 11) and the antisense primer 3'-GAA GAA GCC CCC GTT GCA GCA GTA CAG CCG CTT-5' (SEQ ID NO: 12) at the substitution of the 26th lysine codon AAA with cysteine codon TGC;

sense primer 5'-GGC TTC TTC CTG CGC TGC CAC CCC GAC GGC CGA-3' (SEQ ID NO: 13) and the antisense primer 3'-TCG GCC GTC GGG GTG GCA GCG CAG GAA GAA GCC-5' (SEQ ID NO: 14) at the substitution of the 34th isoleucine codon ATC with cysteine codon TGC;

sense primer 5'-CAC CCC GAC GGC CGA TGC GAC GGG GTC CGG GAG-3' (SEQ ID NO: 15) and the antisense primer 3'-CTC CCG GAC CCC GTC GCA TCG GCC GTC GGG GTG-5' (SEQ ID NO: 16) at the substitution of the 40th valine codon GTT with cysteine codon TGC;

sense primer 5'-GAG AAG AGC GAC CCT TGC ATC AAG CTA CAA CTT-3' (SEQ ID NO: 17) and the antisense primer 3'-AAG TTG TAG CTT GAT GCA AGG GTC GCT CTT CTC-5' (SEQ ID NO: 18) at the substitution of the 50th histidine CAC with cysteine codon TGC;

sense primer 5'-AGC GAC CCT CAC ATC TGC CTA CAA CTT CAA GCA-3' (SEQ ID NO: 19) and the antisense primer 3'-TGC TTG AAG TTG TAG GCA GAT GTG AGG GTC GCT-5' (SEQ ID NO: 20) at the substitution of the 52th lysine codon AAG with cysteine codon TGC;

sense primer 5'-AAC CGT TAC CTG GCT TGC AAG GAA GAT GGA AGA-3' (SEQ ID NO: 21) and the antisense primer 3'-TCT TCC ATC TTC CTT GCA AGC CAG GTA ACG GTT-5' (SEQ ID NO: 22) at the substitution of the 76th methionine codon ATG with cysteine codon TGC;

sense primer 5'-ACC AGT TGG TAT GTG TGC CTG AAG CGA ACT GGG-3' (SEQ ID NO: 23) and the antisense primer 3'-CCC AGT TCG CTT CAG GCA CAC ATA CCA ACT GGT-5' (SEQ ID NO: 24) at the substitution of the 117th alanine codon GCA with cysteine codon TGC;

sense primer 5'-GTT GTG TCT ATC AAA TGC GTG TCT GCT AAC CGT-3' (SEQ ID NO: 25) and the antisense primer 3'-ACG GTT AGC AGA CAC GCA TTT GAT AGA CAC AAC-5' (SEQ ID NO: 26) at the substitution of the 67th glycine codon GGA with cysteine codon TGC;

sense primer 5'-GTG TCT ATC AAA GGA TGC TCT GCT AAC CGT TAC-3' (SEQ ID NO: 27) and the antisense primer 3'-GTA ACG GTT AGC AGA GCA TCC TTT GAT AGA CAC-5' (SEQ ID NO: 28) at the substitution of the 68th valine codon GTG with cysteine codon TGC;

sense primer 5'-ATC AAA GGA GTG TCT TGC AAC CGT TAC CTG GCT-3' (SEQ ID NO: 29) and the antisense primer 3'-AGC CAG GTA ACG GTT GCA AGA CAC TCC TTT GAT-5' (SEQ ID NO: 30) at the substitution of the 70th alanine codon GCT with cysteine codon TGC;

sense primer 5'-AAG GAA GAT GGA AGA TGC CTG GCT TCT AAA TCT-3' (SEQ ID NO: 31) and the antisense primer 3'-AGA TTT AGA AGC CAG GCA TCT TCC ATC TTC CTT-5' (SEQ ID NO: 32) at the substitution of the 82th leucine codon TTA with cysteine codon TGC;

sense primer 5'-GAT GGA AGA TTA CTG TGC TCT AAA TCT GTT ACG-3' (SEQ ID NO: 33) and the antisense primer 3'-CGT AAC AGA TTT AGA GCA CAG TAA TCT TCC ATC-5' (SEQ ID NO: 34) at the substitution of the 84th alanine codon GCT with cysteine codon TGC;

sense primer 5'-TAC AAT ACT TAC CGG TGC AGG AAA TAC ACC AGT-3' (SEQ ID NO: 35) and the antisense primer 3'-ACT GGT GTA TTT CCT GCA CCG GTA AGT ATT GTA-5' (SEQ ID NO: 36) at the substitution of the 108th serine codon TCA with cysteine codon TGC;

sense primer 5'-GGA CCT GGG CAG AAA TGC ATA CTT TTT CTT CCA-3' (SEQ ID NO: 37) and the antisense primer 3'-TGG AAG AAA AAG TAT GCA TTT CTG CCC AGG TCC-5' (SEQ ID NO: 38) at the substitution of the 136th alanine codon GCT with cysteine codon TGC;

sense primer 5'-CCT GGG CAG AAA GCT TGC CTT TTT CTT CCA ATG-3' (SEQ ID NO: 39) and the antisense primer 3'-CAT TGG AAG AAA AAG GCA AGC TTT CTG CCC AGG-5' (SEQ ID NO: 40) at the substitution of the 137th isoleucine codon ATA with cysteine codon TGC;

sense primer 5'-GGG CAG AAA GCT ATA TGC TTT CTT CCA ATG TCT-3' (SEQ ID NO: 41) and the antisense primer 3'-AGA CAT TGG AAG AAA GCA TAT AGC TTT CTG CCC-5' (SEQ ID NO: 42) at the substitution of the 138th leucine codon CTT with cysteine codon TGC; and sense primer 5'-TTT CTT CCA ATG TCT TGC AAG AGC TGA TGA-3' (SEQ ID NO: 43) and the antisense primer 3'-TCA TCA GCT CTT GCA AGA CAT TGG AAG AAA-5' (SEQ ID NO: 44) at the substitution of the 144th alanine codon GCT with cysteine codon TGC.

sense primer 5'-GAG AAG AGC GAC CCT TAT ATC AAG CTA CAA CTT-3' (SEQ ID NO: 45) and the antisense primer 3'-AAG TTG TAG CTT GAT ATA AGG GTC GCT CTT CTC-5' (SEQ ID NO: 46) at the substitution of the 50th histidine codon CAC with tyrosine codon TAT.

Example 5: Production and Purification of bFGF Mutants

Each of the expression plasmids of bFGF mutants was transformed into *E. coli* BL21 (DE3) in the same manner as in Example 2, staked and cultured in 500 ml of LB medium (LB/ampicillin), and purified to obtain bFGF of about 18 KDa in size in the same manner as in Example 3. The amount of mutant thus obtained was variable according to the mutant, and about 4 to 12 mg of bFGF was obtained according to the mutant, and the purity was 98% or over.

Each of the bFGF mutants is provided as follows:

A mutant in which the 69th and 87th cysteines of SEQ ID NO: 1 are substituted with serine, and the 34th isoleucine and the 67th glycine are substituted with cysteine A mutant in which the 69th and 87th cysteines of SEQ ID NO: 1 are substituted with serine, and the 34th isoleucine and the 70th alanine are substituted with cysteine A mutant in which the 69th and 87th cysteines of SEQ ID NO: 1 are substituted with serine, and the 34th isoleucine and the 84th alanine are substituted with cysteine A mutant in which the 69th and 87th cysteines of SEQ ID NO: 1 are substituted with serine, and the 40th valine and 82nd leucine are substituted with cysteine A mutant in which the 69th and 87th cysteines of SEQ ID NO: 1 are substituted with serine, and the 40th valine and 84th alanine are substituted with cysteine A mutant in which the 69th and 87th cysteines of SEQ ID NO: 1 are substituted with serine, and the 50th histidine and the 69th cysteine are substituted with cysteine A mutant in which the 69th and 87th cysteines of SEQ ID NO: 1 are substituted with serine, and the 52nd lysine and the 68th valine are substituted with cysteine A mutant in which the 69th and 87th cysteines of SEQ ID NO: 1 are substituted with serine, and the 76th methionine and 108th serine are substituted with cysteine A mutant in which the 69th and 87th cysteines of SEQ ID NO: 1 are substituted with serine, and the 117th alanine and the 136th alanine are substituted with cysteine.

A mutant in which the 69th and 87th cysteines of SEQ ID NO: 1 are substituted with serine, and the 117th alanine and the 137th isoleucine are substituted with cysteine.

A mutant in which the 69th and 87th cysteines of SEQ ID NO: 1 are substituted with serine, and the 75th alanine is substituted with cysteine.

A mutant in which the 69th and 87th cysteines of SEQ ID NO: 1 are substituted with serine, and the 26th lysine and 87th cysteine are substituted with cysteine.

A mutant in which the 69th and 87th cysteines of SEQ ID NO: 1 are substituted with serine, and the 138th leucine is substituted with cysteine.

A mutant in which the 69th and 87th cysteines of SEQ ID NO: 1 are substituted with serine, and the 52nd lysine and 144th alanine are substituted with cysteine.

A mutant in which the 69th and 87th cysteines of SEQ ID NO: 1 are substituted with serine, the 75th alanine is substituted with cysteine, and the 50th histidine is substituted with tyrosine.

The purification of the wild type and mutant can be purified through SP-sephrose and haparin affinity column. Both species were eluted at about 400 mM NaCl concentration in the SP column and 1.5M NaCl in the heparin column. After progressing the final heparin affinity column purification, SDS Page analysis was performed.

Figure 8:
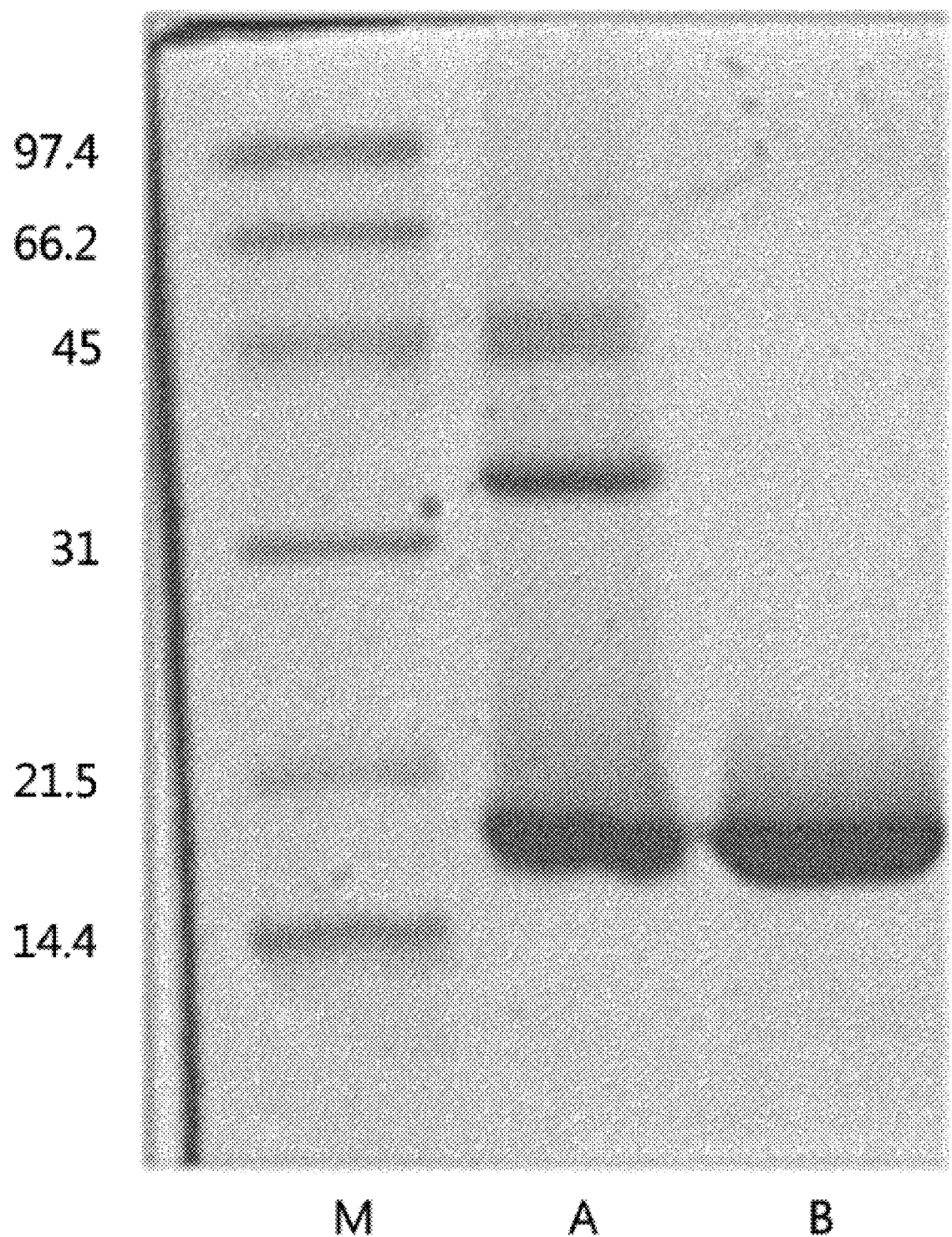
FIG. 8 is an analysis using SDS-PAGE after final purification of wild-type bFGF (A) and bFGF mutant (K75) (B) of the present disclosure.

As illustrated in FIG. 8, dimer and trimer were observed in the case of the wild type, whereas it was confirmed that the mutant existed in the form of a single band in the monomer size. It can be seen that the dimer and trimmer with no activity are completely removed and exist in the monomer state.

FIG. 8 illustrates SDS-PAGE results of the wild type (A) and mutant (B) after final purification.

Experimental Example 1: Structural Analysis of Wild Type and Mutant bFGF Using Circular Dichroism The structure and thermal stability of the purified bFGF mutants of Example 5 were measured by circular dichroism analysis using a J-810 spectrometer (JASCO). The wild-type bFGF was purified using the purified bFGF in Example 3. For structural analysis, each bFGF is dissolved in 20 mM sodium phosphate (pH 7.0), and the final concentration is adjusted constantly to 0.1 mg/ml. Then, the structure was analyzed under the conditions that it was put in a 0.1 cm cell, and in 190 nm to 250 nm region, the band width was 1 nm, the response was 0.25 sec, the data pitch was 0.1 nm, the scanning speed was 20 nm/min, the cell length was 1 cm, the accumulation was 8 times, and the temperature was 20° C.

In order to analyze thermal stability, Tm (melting temperature) was compared with far-UV at 20° C. and 95° C. to determine the wavelength of 208 nm and 0.1 mg/ml concentration in 0.1 cm cell. Conditions were measured at 20° C. to 95° C. under the condition of 1° C./min. The results are exhibited in Table 2.

TABLE 2

| Mutant bFGF Name | Structure change (Tm) | Mutant bFGF Name | Structure change (Tm) | Mutant bFGF Name | Structure change (Tm) |
|---|---|---|---|---|---|
| Wild-type bFGF (SEQ ID NO.: 1) | –(57.5° C.) | Mutant A34-67 | Reduced 48 | Mutant B34-70( | No change |
| Mutant C34-84 | No change | Mutant D40-82 | No change | Mutant E40-84 | No change |
| Mutant F50-69 (SEQ ID NO.: 8) | No change | Mutant G52-68 (SEQ ID NO.: 9) | No change | Mutant H76-108 | No change |
| Mutant I117-136 | No change | Mutant J117-137 | No change | Mutant K75 | Change (62° C.) |
| Mutant L26-87 Mutant K75 + H50Y | No change (65° C.) | Mutant M138 | No change | Mutant N52-144 | No change |

Table 2 exhibits the results of measurement of the degree of structural change for wild-type bFGF and bFGF mutants and the fraction unfolded per temperature at a wavelength of 208 nm in a circular dichroism analysis for measuring thermal stability. When the folding-loosening phenomenon occurs, the structure changes in the region around 208 nm is exhibited. Using this, the accurate Tm value was analyzed by measuring the melting temperature TM within the range of 20 to 95° C.

The bFGF mutants are mutants in which the 69th and 87th cysteines of SEQ ID NO: 1 are substituted with serine, and further, the residues at the respective corresponding locations are substituted with cysteines to induce intramolecular disulfide bonds.

As a result, most of the structural changes exhibited the same structure as that of wild-type bFGF, and there was no change, and the mutants added with disulfide bonds had no specific structure. The Tm, which exhibits a thermal stability, is identical to that of the most bFGF mutants as compared to the wild-type bFGF at 58° C. Among them, the heat stability was improved up to 62° C. in the K75 mutant. This means that the thermal stability is increased by artificially adding disulfide bonds by substituting one amino acid with cysteine.

Meanwhile, in order to confirm the conspicuousness of the K75 mutant having the 69th and 87th cysteines of SEQ ID NO: 1, which are specific positions of the present disclosure, substituted with serine and the 75th alanine further substituted with cysteine, the thermal stability of the wild-type bFGF of SEQ ID NO: 1, the bFGF mutant (Cys→Ser mutant) in which only the 69th and 87th cysteines of SEQ ID NO: 1 were substituted with serine, the a bFGF mutant (wild type+disulfide bond) in which only the 75th alanine of SEQ ID NO: 1 was substituted with the cysteine and the K75 mutant (Cys→Ser mutant+disulfide bond, the bFGF mutant in which the 69th and 87th cysteines of SEQ ID NO: 1 were substituted with serine, and the 75th alanine was substituted with cysteine) was compared and confirmed.

Figure 5:
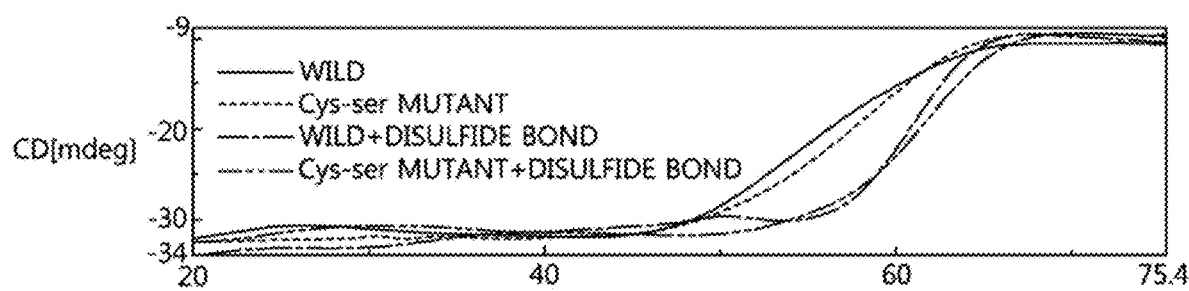
FIG. 5 illustrates the results of the difference in the melting temperature (TM), which is an index of the thermal stability of the wild-type bFGF and the bFGF mutant of the present disclosure.

As a result, as illustrated in FIG. 5, it was confirmed that the TM of the wild-type bFGF was about 57.5° C., the TM of the Cys→Ser mutant was 58° C., the TM of the wild type+disulfide bond was 61.5° C., the TM of K75 mutant (Cys→Ser mutant+disulfide bond) was at 62° C., indicating that the thermodynamic stability of the K75 mutant was increased.

In a further experiment, it was confirmed that the TM of thermal stability of HsbFGF in which the 69th and 87th cysteines of SEQ ID NO: 1 were substituted with serine, and the 50th histidine was substituted with tyrosine in the K75 mutant in which the 75th alanine was further substituted with cysteine was improved up to 65° C. compared to the wild-type bFGF at 58° C. and K75 mutant at 62° C. This means that one amino acid existing on the surface is substituted with tyrosine to stabilize the cavity inside the protein, and the thermal stability due to the newly formed hydrogen bond and van deer waals interaction is increased.

Figure 9:
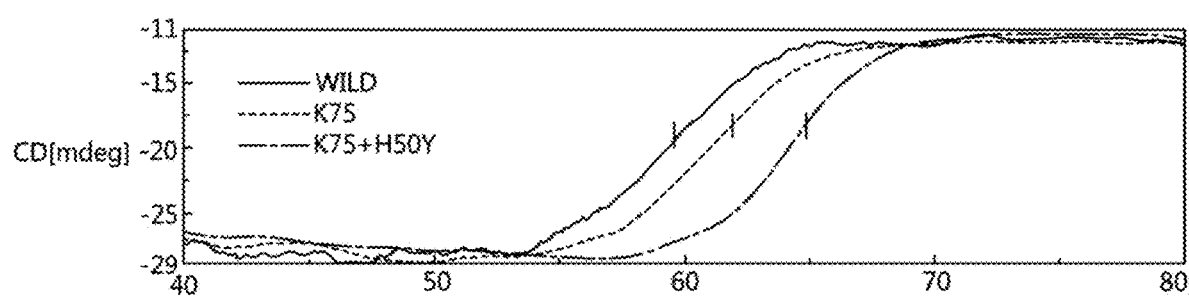
FIG. 9 illustrates the results of the difference of TM (Melting temperature), which is an index of the thermal stability of the wild-type bFGF, the sbFGF mutant of the present disclosure, and HsbFGF.

As a result, as illustrated in FIG. 9, it was confirmed that the TM of the wild-type bFGF was about 57.5° C., the TM of K75 mutant (Cys→Ser mutant+disulfide bond) was 62° C., and HsbFGF (K75+His→Tyr) TM means that the thermodynamic stability of the mutant is increased at 65° C.

Figure 6:
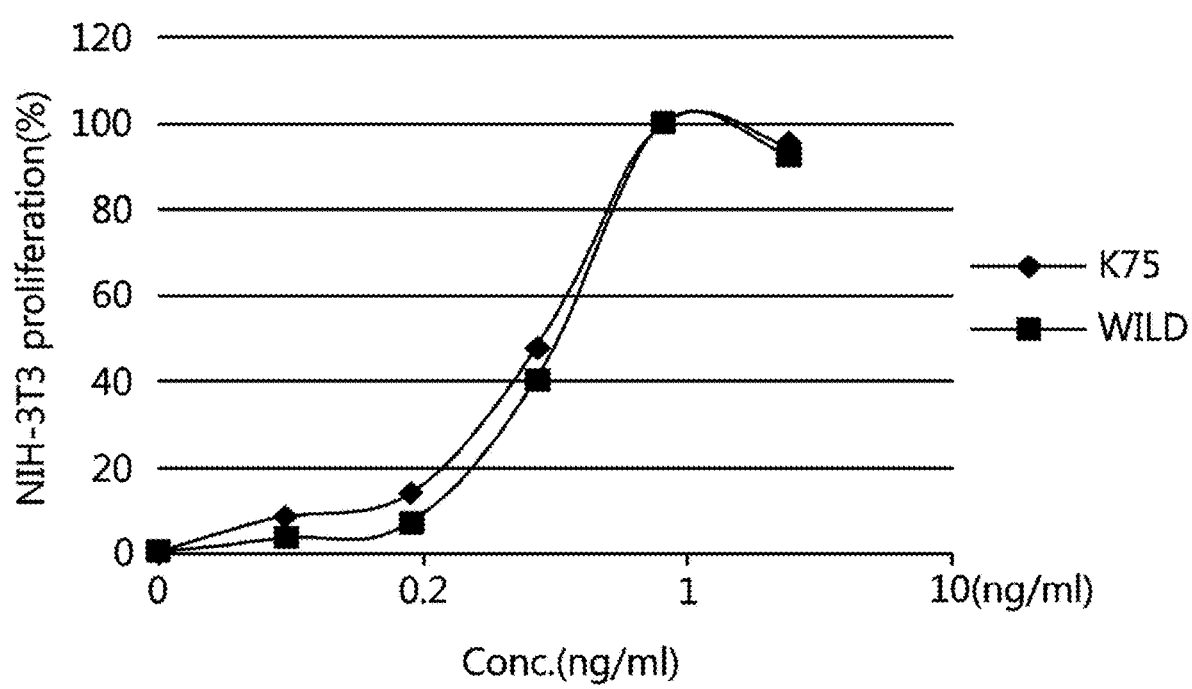
FIG. 6 illustrates the results of comparing the activity of wild-type bFGF with the bFGF mutant of the present disclosure.
Figure 12:
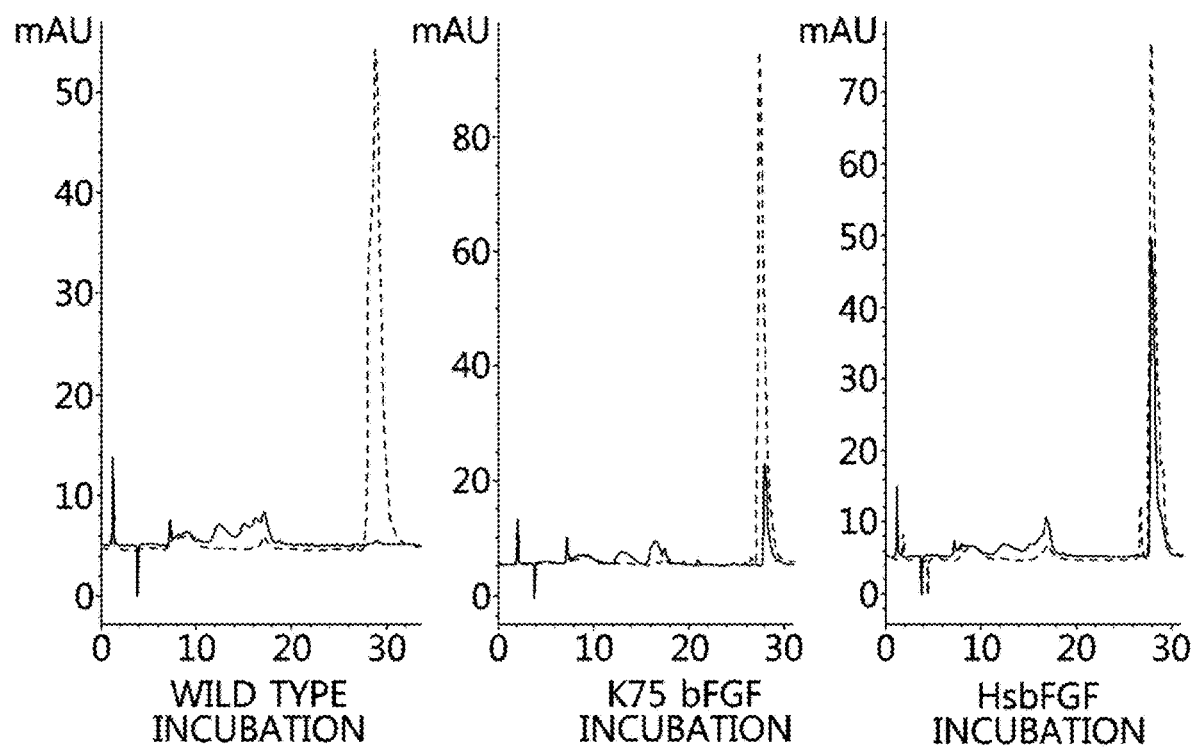
FIG. 12 illustrates HPLC quantitative comparison results after 5 days of incubation at 60° C. in PBS (Phosphate buffer saline) conditions, which are the most similar to the wild-type bFGF and the bFGF mutant of the present disclosure and HsbFGF human body conditions.
Figure 13:
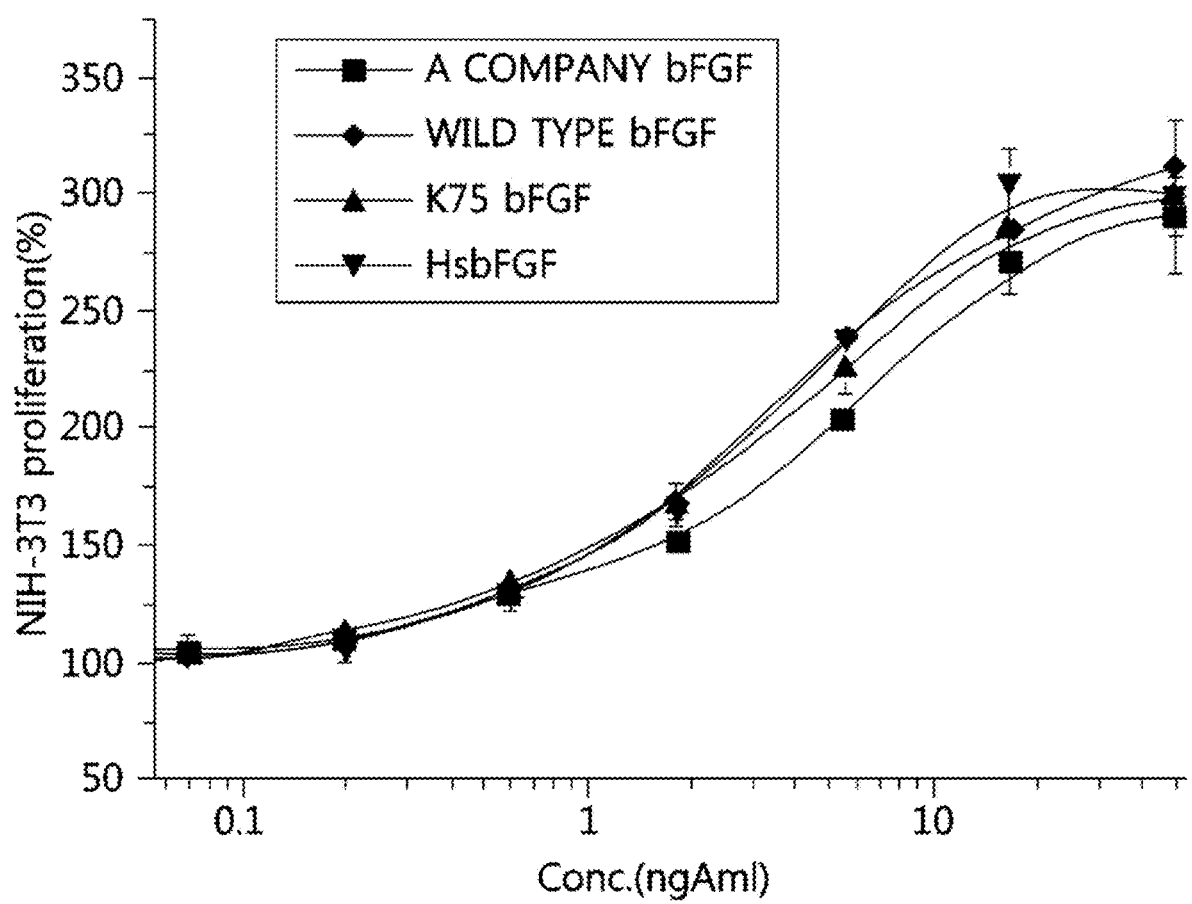
FIG. 13 illustrates the results of comparing the bFGF activities of the wild-type bFGF and the bFGF mutants of the present disclosure.

Experimental Example 2: Examination of Cell Proliferation of Wild-Type and Mutant bFGF The made wild-type bFGF and bFGF mutants having the structure of using solubility and circular dichroism and showing good results through the result analysis of TM were selected to perform a cell proliferation examination. Cell proliferation examinations were entrusted to Genewel Inc., and were performed with NIH3T3 cell line, a skin cell sensitive to bFGF. As an experiment method, NIH-3T3 cells were maintained in DMEM complete medium including 10% heat-inactivated fetal bovine serum, 100 units/ml penicillin, and 100 mg/ml streptomycin. NIH-3T3 cells of 2×10³ cells/well were seeded in a 96 well culture plate. 24-hour-cultured NIH-3T3 cells were treated with serum-free DMEM medium and treated with sample solution in DMEM medium including 0.5% FBS per each concentration after starvation, and then was cultured for 72 hours. After culturing, 10 µl of MTT [3-(4,5-dimethylthiazol-2-yl)-2,5-diphenyl-2H-tetrazolium bromide] solution was added and reacted for 2 hours. 100 µl of DMSO was used to dissolve formazan crystal. Absorbance was measured at a wavelength of 540 nm using a spectrophotometer. The susceptibility to the drug was compared by the percentage of the absorbance of the untreated well (control) in the drug treated wells. As illustrated in FIGS. 6 and 12, the bFGF mutant exhibits cell proliferation ability similar to that of the wild-type bFGF.

Experimental Example 3: Quantitative Analysis of Protein by Incubation of Wild-Type and Mutant bFGF In order to confirm the stability of the wild-type bFGF and mutants [bFGF mutant (Cys→Ser mutant) in which only the 69th and 87th cysteine of SEQ ID NO: 1 were substituted with serine, bFGF mutant in which only the 75th alanine of SEQ ID NO: 1 was substituted with cysteine (wild type+disulfide bond) and the K75 mutant (Cys→Ser mutant+disulfide bond, bFGF mutant in which the 69th and 87th cysteines of SEQ ID NO: 1 were substituted with serine and the 75th alanine was substituted with cysteine), 37° C. short-term incubation test was performed. In the state of PBS (phosphate buffer saline), which is the most similar to the human body, the wild-type bFGF and its mutants were dissolved at 0.5 mg/ml and incubated in a water bath at 37° C. They were sampled in the unit of 48 hours, 7 days, and 10 days and centrifuged at 13000 rpm for 15 minutes at 4° C. to obtain only supernatant. Proteins were quantified using Nano drop. As time goes by, the concentrations of wild-type bFGF and mutants were quantitatively determined, and the wild-type bFGF exhibited a more significant decrease than the mutant. The results are exhibited in Table 3.

TABLE 3

| bFGF name | Day 0 | After 48 h | After one week | After 10 days |
|---|---|---|---|---|
| Wild type | 100 | 56 | 26 | 16 |
| CYS → SER mutant | 100 | 88 | 80 | 62 |
| Wild type + disulfide | 100 | 92 | 78 | 64 |
| K75 (CYS → SER mutant + disulfide bond) | 100 | 90 | 88 | 80 |

In addition, based on the above results, the determination of whether the K75 mutant had long-term storage stability in comparison with the wild-type bFGF in the PBS (phosphate buffer saline) state, which is the most similar to the human body using the K75 mutant having increased thermal stability was confirmed. First, the wild-type bFGF and K75 mutants were dissolved in PBS (phosphate buffer saline) at the same concentration, followed by incubation at 25° C. for 20 days. After centrifugation, the supernatant was quantitatively analyzed using HPLC.

Figure 7:
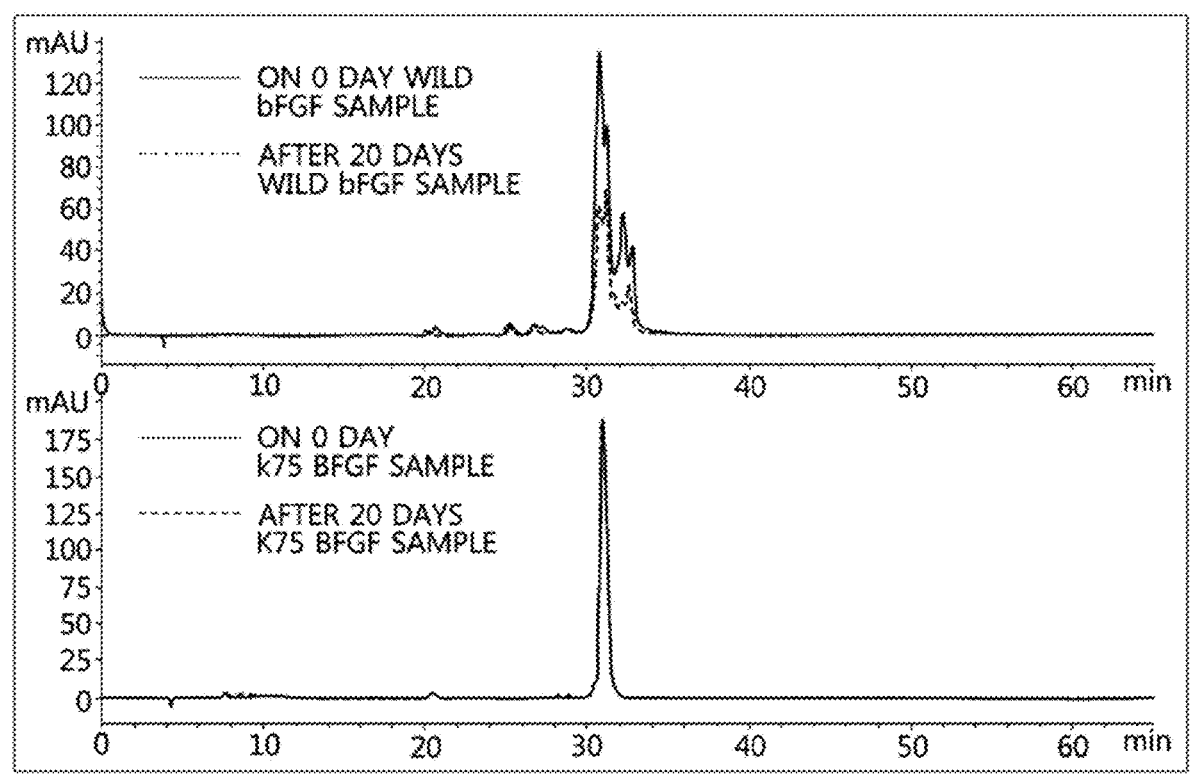
FIG. 7 illustrates the results of stability comparison after 20 days of incubation at 25° C. in PBS (phosphate buffer saline) conditions, which are the most similar to the human body conditions of wild-type bFGF and the bFGF mutant of the present disclosure.

As a result, as illustrated in FIG. 7, the K75 mutant during the incubation was much more stable than the wild-type bFGF, which is a result of demonstrating the superiority of the K75 mutant of the present disclosure.

Experimental Example 4: HPLC Analysis of Wild-Type and Mutant bFGFs at 50 and 60° C. Cincubation In order to confirm the stability of the wild-type bFGF and K75 mutants (Cys→Ser mutant+disulfide bond, bFGF mutant in which the 69th and 87th cysteines of SEQ ID NO: 1 were substituted with serine and the 75th alanine was substituted with cysteine) and the HsbFGF K75 mutant (Cys→Ser mutant+disulfide bond, bFGF mutant in which the 69th and 87th cysteines of SEQ ID NO: 1 were substituted with serine, the 75th alanine was substituted with cysteine, and the 50th histidine was substituted with tyrosine), the incubation test was performed for a week at 50° C. and for 5 days at 60° C. Each of the wild-type bFGF and its mutants were dissolved in PBS (phosphate buffer saline) at 0.5 mg/ml and incubated in a water bath at 50° C. and 60° C. The samples according to the dates were centrifuged at 13000 rpm for 15 min at 4° C. to obtain only supernatant, and the protein was analyzed by using HPLC and UV spectrometer.

Figure 10:
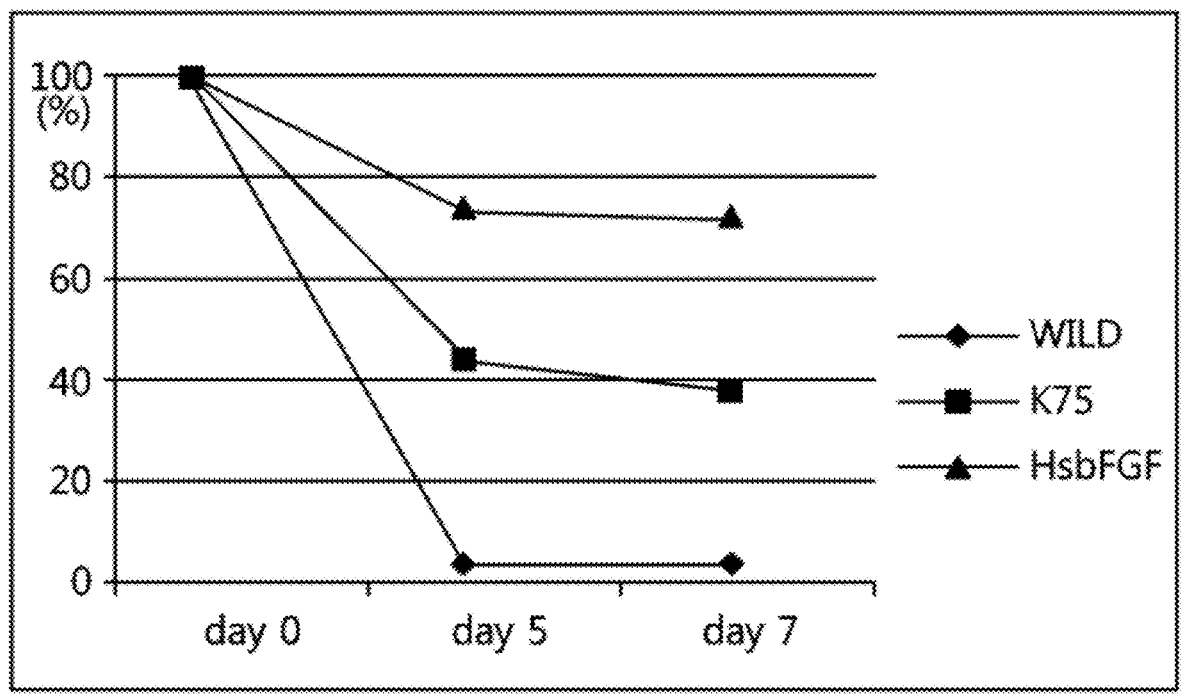
FIG. 10 illustrates the stability comparison results after one week of incubation at 50° C. in PBS (Phosphate buffer saline) conditions, which are the most similar to the sbFGF mutant and HsbFGF human body conditions of the present disclosure.

As a result, as illustrated in FIG. 10, in the quantification using the UV spectrometer, the wild-type bFGF could not be quantified after 5 days. In the case of the K75 mutant, 38% remained after 7 days and 72% in the case of hsbFGF was maintained.

Figure 11:
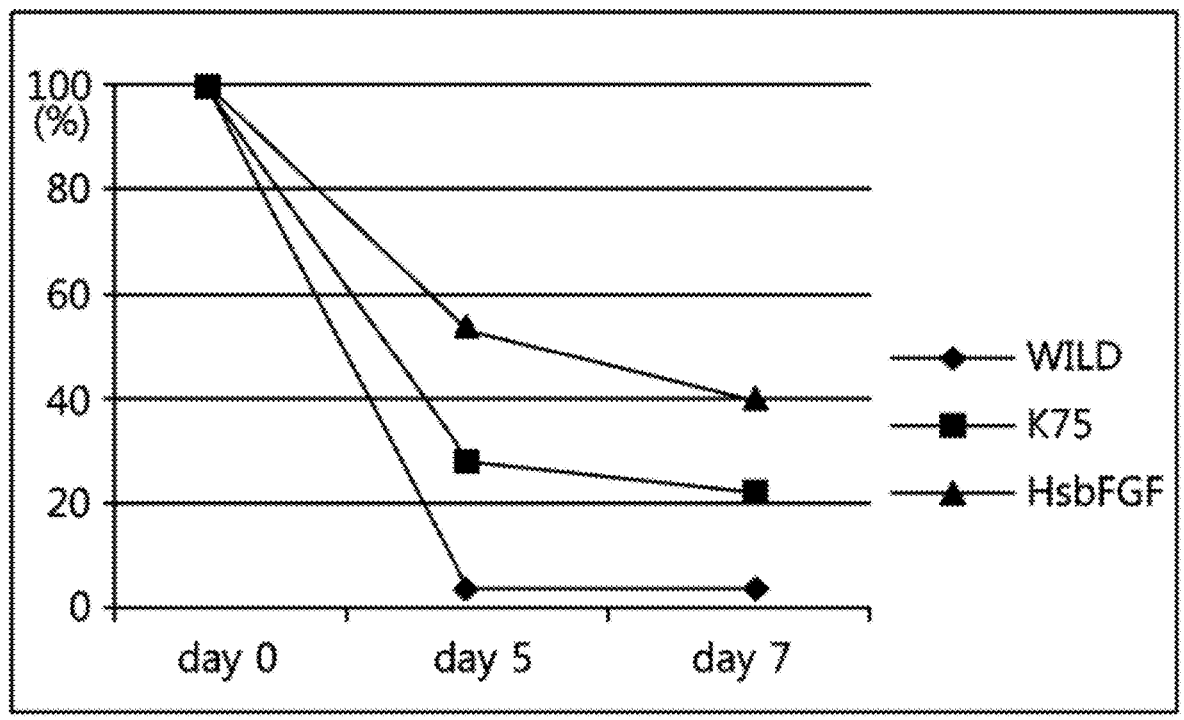
FIG. 11 illustrates the stability comparison results after 5 days of incubation at 60° C. in PBS (Phosphate buffer saline) conditions, which are the most similar to the wild-type bFGF and the bFGF mutant of the present disclosure and HsbFGF human body conditions.

Also, as illustrated in FIG. 11, in the case of quantification using a 60° C. UV spectrometer, almost no wild-type bFGF was detected from the third day on. In case of K75, only 22% remained after 5 days. In case of HsbFGF, 40% was maintained after 5 days.

In the HPLC analysis using the results illustrated in FIG. 12, the wild-type bFGF could not be quantified with HPLC after 7 days. In case of K75, it was confirmed that 60% or more was remained in case of 30% HsbFGF.

The invention claimed is:

1. A basic fibroblast growth factor (bFGF) mutant, wherein the mutant is a bFGF mutant in which the 69th and 87th cysteines of SEQ ID NO: 1 are substituted with serine, the 75th alanine of SEQ ID NO: 1 is substituted with cysteine, and the 50th histidine of SEQ ID NO: 1 is substituted with tyrosine.

* * * * *